United States Patent
Ding et al.

(10) Patent No.: US 10,745,367 B2
(45) Date of Patent: Aug. 18, 2020

(54) METHOD FOR PREPARING FORMAMIDE COMPOUND

(71) Applicant: SHANGHAI GREENCARBON HI-TECH CO., LTD., Shanghai (CN)

(72) Inventors: Kuiling Ding, Shanghai (CN); Lei Zhang, Shanghai (CN); Zhaobin Han, Shanghai (CN); Zheng Wang, Shanghai (CN); Xiaoyu Zhao, Shanghai (CN)

(73) Assignee: SHANGHAI GREENCARBON HI-TECH CO., LTD., Shanghai (CN)

( * ) Notice: Subject to any disclaimer, the term of this patent is extended or adjusted under 35 U.S.C. 154(b) by 0 days.

(21) Appl. No.: 15/551,705

(22) PCT Filed: Jan. 27, 2016

(86) PCT No.: PCT/CN2016/072342
§ 371 (c)(1),
(2) Date: Aug. 17, 2017

(87) PCT Pub. No.: WO2016/131371
PCT Pub. Date: Aug. 25, 2016

(65) Prior Publication Data
US 2018/0030009 A1 Feb. 1, 2018

(30) Foreign Application Priority Data

Feb. 17, 2015 (CN) .......................... 2015 1 0086625

(51) Int. Cl.
*C07D 295/185* (2006.01)
*C07C 231/10* (2006.01)
(Continued)

(52) U.S. Cl.
CPC ........ *C07D 295/185* (2013.01); *B01J 31/189* (2013.01); *B01J 31/24* (2013.01);
(Continued)

(58) Field of Classification Search
None
See application file for complete search history.

(56) References Cited

U.S. PATENT DOCUMENTS 8,524,915 B2  9/2013  Schleth et al.
9,000,212 B2  4/2015  Touge et al.
(Continued)

FOREIGN PATENT DOCUMENTS

CN  102247890 A  11/2011
CN  102858749 A  1/2013
(Continued)

OTHER PUBLICATIONS

Rezayee ("Tandem Amine and Ruthenium-Catalyzed Hydrogenation of CO2 to Methanol" J. Am. Chem. Soc., 137, p. 1028-1031, published Jan. 16, 2015; including Supporting Information (SI), p. S1-S15) (Year: 2015).*

(Continued)

*Primary Examiner* — Amy C Bonaparte
(74) *Attorney, Agent, or Firm* — Millen White Zelano and Branigan, PC; Csaba Henter

(57) ABSTRACT

Disclosed is a method for preparing a formamide compound, the method uses carbon dioxide, hydrogen and an amine compound as raw materials and a transition metal complex as a catalyst, and the reaction is carried out in an organic solvent or in the absence of a solvent to form a formamide compound. The method of the present invention is an effective method of chemical utilization of carbon dioxide, which has the advantages of high reaction efficiency, a good selectivity, mild conditions, economic and environmental protection, being simple and convenient to operate and the like, and has a good popularization and application prospect.

8 Claims, 1 Drawing Sheet

(51) Int. Cl.
  *C07D 213/40* (2006.01)
  *C07C 211/14* (2006.01)
  *B01J 31/24* (2006.01)
  *C07F 15/00* (2006.01)
  *C07C 233/03* (2006.01)
  *C07F 9/50* (2006.01)
  *C07C 233/18* (2006.01)
  *B01J 31/18* (2006.01)
  *C07D 207/06* (2006.01)

(52) U.S. Cl.
  CPC ......... *B01J 31/2404* (2013.01); *C07C 211/14* (2013.01); *C07C 231/10* (2013.01); *C07C 233/03* (2013.01); *C07C 233/18* (2013.01); *C07D 207/06* (2013.01); *C07D 213/40* (2013.01); *C07F 9/50* (2013.01); *C07F 15/00* (2013.01); *C07C 2601/14* (2017.05)

(56) References Cited

U.S. PATENT DOCUMENTS

| | | | |
|---|---|---|---|
| 9,012,690 B2 | 4/2015 | Ogata et al. | |
| 2013/0041160 A1 | 2/2013 | Schleth et al. | |
| 2013/0172619 A1 | 7/2013 | Ogata et al. | |
| 2014/0303374 A1 | 10/2014 | Touge et al. | |
| 2015/0105571 A1* | 4/2015 | Jackstell | C07C 231/10 556/7 |

FOREIGN PATENT DOCUMENTS

| | | | | |
|---|---|---|---|---|
| CN | 103237779 A | 8/2013 | | |
| CN | 103492351 A | 1/2014 | | |
| CN | 103702968 A | 4/2014 | | |
| CN | 103864852 A | 6/2014 | | |
| DE | 102012019441 A1 * | 4/2013 | ........... | C07C 231/10 |

OTHER PUBLICATIONS

Kuriyama ("Catalytic Hydrogenation of Esters. Development of an Efficient Catalyst and Processes for Synthesising (R)-1,2-Propanediol and 2-(I-Menthoxy)ethanol)" Organic Process Research and Development, 2012, 16, p. 166-171) (Year: 2012).*
Oldenhuis ("Catalytic acceptorless dehydrogenations: Ru-Macho catalyzed construction of amides and imines" Tetrahedron 70, 2014, p. 4213-4218; including SI, p. S1-S22) (Year: 2014).*
Strem ("Ruthenium (CAS No. 1295649-40-9): Strem Product Catalog", p. 1, downloaded from https://www.strem.com/catalog/v/44-0071/59/ruthenium_1295649-40-9 on Jul. 24, 2018) (Year: 2018).*
Federsel ("A Well-Defined Iron Catalyst for the Reduction of Bicarbonates and Carbon Dioxide to Formates, Alkyl Formates, and Formamides" Angew. Chem. Int. Ed., 2010, 49, p. 9777-9780) (Year: 2010).*
Tlili ("Reductive functionalization of CO2 with amines: an entry to formamide, formamidine, and methyl derivatives" Green Chemistry, 2015, 17, p. 157-168) (Year: 2015).*
International Search Report for PCT/CN2016/072342 dated May 4, 2016.
Morass!, R. et al., "Five-co-ordination with 'Hybrid' Ligands. Part VII. Colbalt(II) and Nickel(II) complexes with Asymmetric Tripod Ligands having N2OP, N2SP, and NOAs2 Donor Sets," J. Chem. Soc. (A) Inorg. Phys. Theor., Jan. 1, 1971, No. 10, pp. 1487-1491.
English Abstract of CN103702968, Publication Date: Apr. 2, 2014.
English Abstract of CN102247890, Publication Date: Nov. 23, 2011.
English Abstract of CN103864852, Publication Date: Jun. 18, 2014.

* cited by examiner

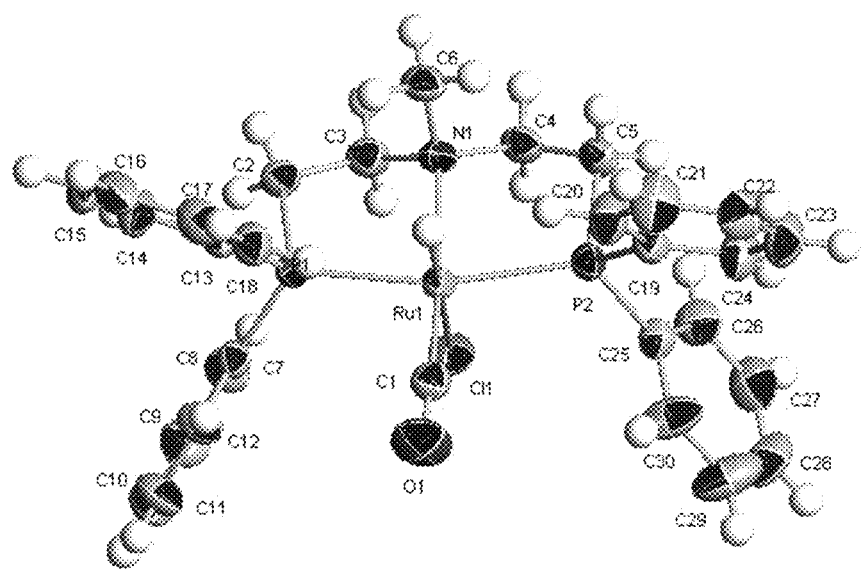

METHOD FOR PREPARING FORMAMIDE COMPOUND

FIELD OF THE INVENTION

The present invention relates to the field of organic synthesis and catalysis. More specifically, the present invention relates to a process for the preparation of formamide compounds by using clamped transition metal complexes as catalysts to perform the reaction between carbon dioxide, hydrogen and an amine compound.

BACKGROUND OF THE INVENTION

Carbon dioxide is a greenhouse gas that affects the environment as well as an inexhaustible, cheap, safe and renewable carbon resource. In recent years, how to provide useful chemistry and chemical engineering products by using carbon dioxide as a carbon resource has attracted wide concern of governments and scientists while in-depth study has been carried out.

On the other hand, formamide compounds such as formamide, N, N-dimethylformamide (DMF) and N-formylmorpholine are very important chemical raw materials, solvents and pharmaceutical intermediates in which DMF is referred to as "universal solvent" which can also be used in the petrochemical industry as a gas absorbent for the separation and refining of gas; in addition, N-formyl morpholine is also an important formamide compound has a wide range of applications in industry, which can be used as a solvent in organic synthesis as well as the best extraction solvent for the separation of aromatic hydrocarbons and paraffin hydrocarbons to produce benzene with high purity (99.99%).

Commonly used methods to produce formamides in industry are formic acid method, methyl formate method, etc. The method for DMF is relatively special, which is mainly a carbon monoxide method, in which the main raw materials are synthesis ammonia, industrial methanol and carbon monoxide. At present, the raw materials for this method are of wide range of source, thus suitable for large-scale continuous production. Most of the large enterprises in United States, Japan and China use this method. However, in consideration of the large production and consumption of DMF, and the method based on non-renewable coal resources as raw material, the development of cleaner and reproducible production method is still necessary.

DMF can also be synthesized from $CO_2$ as raw material, and formic acid obtained by hydrogen reduction of $CO_2$ reacts with dimethylamine and is dehydrated to give DMF. But the catalyst developed later is of low efficiency, of which TON is 3400. Until 1994, Prof. NOYORI found that DMF can be synthesised in the supercritical carbon dioxide with tetra (trimethylphosphine) dichloro ruthenium complex as a catalyst at high efficiency, of which TON reached 4.2 million, but the total pressure of the supercritical reaction system is up to 210 atmospheric pressure, not only leading to high energy consumption, but also harsh requirement to the equipment and materials, so that the catalytic system is not suitable for practical applications in the industry. At the same time, the method is of poor substrate applicability due to the different solubility of amine in the supercritical carbon dioxide. Only a few formamide compounds can be synthesized in this way, such as dimethylamine, diethylamine and propylamine. In 2012, Prof. Cantat reported that polysilicate reagent can be used to reduce $CO_2$ and reacts with several primary amine and secondary amine to prepare DMF and other formamide compounds. However, this method requires the use of equivalent amounts of silicon reagent which is of high cost, and when the substrate is a primary amine, it is prone to be over reduced, and of poor reaction selectivity.

Therefore, there is a need in the art for a new environmental friendly method for synthesizing formamide compounds which is of good substrate applicability, convenient use of catalyst, high production efficiency and suitable reaction conditions for industrial production, and low by-product pollution.

SUMMARY OF THE INVENTION

The object of the present invention is to provide a new method for the preparation of a formamide compound.

In the first aspect of the present invention, a method for the preparation of a formamide compound is provided, wherein the method comprises following steps:

(A) reacting an amine compound of formula I with carbon dioxide and hydrogen under the action of catalyst III to form a formamide compound of formula II:

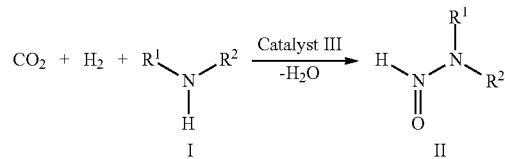

wherein, $R^1$ is selected from a hydrogen, substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8;

$R^2$ is selected from a substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8; wherein, $R^3$, $R^4$, $R^5$ are independently selected from a hydrogen, substituted or unsubstituted $C_1$-$C_{20}$ alkyl, substituted or unsubstituted $C_6$-$C_{24}$ aryl, substituted or unsubstituted $C_7$-$C_{25}$ arylalkyl or heteroaryl, wherein $R^4$ and $R^5$ can connect to form a substituted or unsubstituted $C_3$-$C_{10}$ cycloalkyl, $C_4$-$C_{24}$ aryl or heteroalkyl, wherein the "substituted" means that one or more hydrogen atoms of a group is substituted by a substitutent selected from the following group: a hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, amido.

In another preferred embodiment, the catalyst is a pincer catalyst having a structure represented by the general formula III:

$$M(L)XYY' \qquad (III)$$

wherein,

M is selected from Group VIIIB transition metals; Fe, Co, Ni, Ru, Rh, Pd, Os, Ir, Pt, or the combinations thereof;

X, Y and Y' are independently selected from a group consisting of carbon monoxide, triphenylphosphine, pyridine, tetrahydrofuran, dimethylsulfoxide or hydrogen anion, hydroxide, chloride ion, bromide ion, iodide ion, $BH_4^-$, $BH_3CN^-$, $BH(Et)_3^-$, $BH(sec-Bu)_3^-$ or $AlH_4^-$;

L is a tridentate pincer ligand as shown in Formula IV,

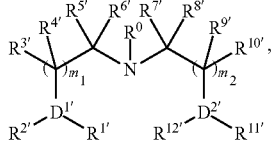

IV wherein, $m_1$ and $m_2$ are independently an integer selected from 1-3;

$D^{1'}$ and $D^{2'}$ are electron donor atoms coordinated to a metal atom, which are independently selected from the group consisting of P, N and S;

$R^0$ is selected from a hydrogen, substituted or unsubstituted $C_1$-$C_{10}$ alkyl, substituted or unsubstituted $C_3$-$C_{10}$ cycloalkyl, substituted or unsubstituted $C_6$-$C_{24}$ aryl, substituted or unsubstituted $C_7$-$C_{25}$ arylalkyl, substituted or unsubstituted $C_4$-$C_{20}$ heteroaryl;

$R^{1'}$, $R^{2'}$, $R^{11'}$ and $R^{12'}$ are independently selected from a hydrogen, substituted or unsubstituted $C_1$-$C_{10}$ alkyl, substituted or unsubstituted $C_3$-$C_{10}$ cycloalkyl, substituted or unsubstituted $C_4$-$C_{24}$ aryl or heteroaryl, wherein the $R^{1'}$ and $R^{2'}$, or $R^{11'}$ and $R^{12'}$ can connect to form a $C_3$-$C_{10}$ cycloalkyl, $C_4$-$C_{24}$ aryl or heteroalkyl;

$R^{3'}$, $R^{4'}$, $R^{5'}$, $R^{6'}$, $R^{7'}$, $R^{8'}$, $R^{9'}$ and $R^{10'}$ are independently selected from a group consisting of: a hydrogen, substituted or unsubstituted $C_1$-$C_{10}$ alkyl, $C_3$-$C_{10}$ cycloalkyl, substituted or unsubstituted $C_1$-$C_{10}$ alkoxy or $C_6$-$C_{36}$ aryl, wherein $R^{3'}$, $R^{4'}$, $R^{5'}$, $R^{6'}$, $R^{7'}$, $R^{8'}$, $R^{9'}$ and $R^{10'}$ can be connected with each other to form a substituted or unsubstituted $C_3$-$C_{10}$ aliphatic cycloalkyl, $C_4$-$C_{24}$ aryl or heteroaryl group;

wherein the "substituted" means that one or more hydrogen atoms of a group is substituted by a substitutent selected from the following group: a hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, amido.

In another preferred embodiment, the amine compound is an organic primary amine or an organic secondary amine compound.

In another preferred embodiment, the preferred $R^0$ is selected from a group consisting of H, $C_1$-$C_4$ alkyl (e.g., methyl) or phenyl.

In another preferred embodiment, preferred $R^{1'}$, $R^{2'}$, $R^{11'}$, $R^{12'}$ are independently selected from a group consisting of: phenyl, ethyl, isopropyl, t-butyl, cyclohexyl or adamantane.

In another preferred embodiment, $R^{3'}$, $R^{4'}$, $R^{5'}$, $R^{6'}$, $R^{7'}$, $R^{8'}$, $R^{9'}$, $R^{10'}$ are independently selected from a hydrogen, phenyl or pyridyl.

In another preferred embodiment, M is Ru or Ir.

In another preferred embodiment, the catalyst is a complex of the following structure:

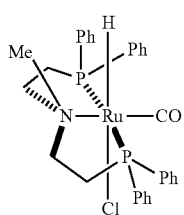

1a

-continued

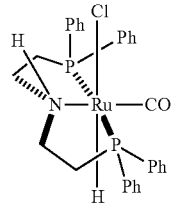

1b

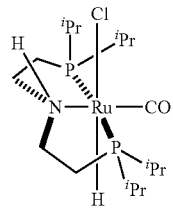

1c

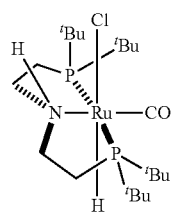

1d

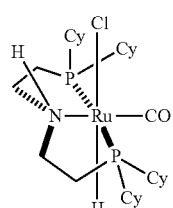

1e

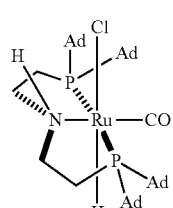

1f

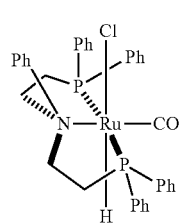

1g

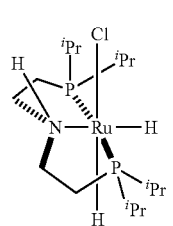

1h

-continued

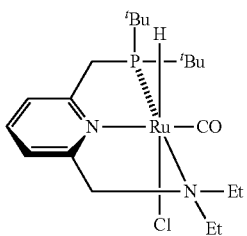

2a

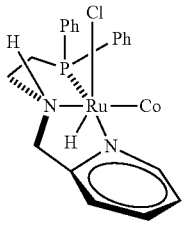

2b

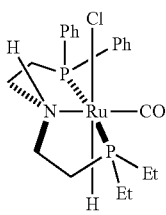

2c

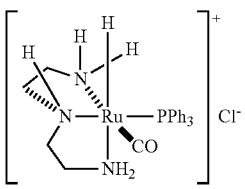

2d

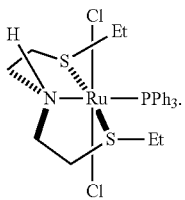

3a

In another preferred embodiment, the catalyst is ruthenium complex.

In another preferred embodiment, the molar ratio of the organoamine compound to the catalyst is 1000-5600000:1.

In another preferred embodiment, the molar ratio of the organoamine compound to the catalyst is 10000-4000000:1, preferably from 50000-2500000:1.

In another preferred embodiment, in step a), a base additive is further used, wherein the base additive is selected from a group consisting of alkali metal salts of alcohols, alkali metal carbonates of alcohols, alkali metal hydroxides, or combinations thereof.

In another preferred embodiment, the base additive is potassium tert-butoxide.

In another preferred embodiment, the base additive is not used in step (a).

In another preferred embodiment, the reaction time of the process is from 0.1 to 1000 hours.

In another preferred embodiment, the reaction time of the process is from 2 to 160 hours, preferably from 2 to 120 hours.

In another preferred embodiment, the pressure of hydrogen in the process is from 1 to 100 atmospheres, and/or
The pressure of carbon dioxide is 1-100 atmospheres.

In another preferred embodiment, the pressure of hydrogen in the reaction is from 5 to 40 atmospheres, preferably 35 atmospheres.

In another preferred embodiment, the pressure of carbon dioxide in the reaction is from 5 to 40 atmospheres, preferably 35 atmospheres.

In another preferred embodiment, the reaction is carried out under 60-200° C.

In another preferred embodiment, the reaction is carried out under 80 to 150° C., preferably 80 to 140° C.

In another preferred embodiment, the reaction is carried out in an organic solvent; wherein the organic solvent is selected from a group consisting of DMF, tetrahydrofuran, 2-methyltetrahydrofuran, dioxane, ethylene glycol dimethyl ether, t-butyl methyl ether, benzene, toluene, xylene, methanol, ethanol, isopropanol, t-butanol, or combinations thereof.

In another preferred embodiment, the organic solvent is DMF, tetrahydrofuran, dioxane, toluene, methanol, or a combination thereof.

In another preferred embodiment, the reaction is carried out under solvent-free conditions.

In another preferred embodiment, preferred $R^0$, $R^1$, $R^2$, $R^{3'}$, $R^{4'}$, $R^{5'}$, $R^{6'}$, $R^{7'}$, $R^{8'}$, $R^{9'}$, $R^{10'}$, $R^{1'}$, $R^{2'}$, $R^{11'}$, $R^{12'}$ are the corresponding groups of the specific compounds of the examples in the specification.

In the second aspect of the present invention, a process for the preparation of formamide compounds is provided, wherein the process comprises a step of reacting (i) an organic primary or organic secondary amine compound with (ii) carbon dioxide and (iii) hydrogen under the action of a pincer transition metal catalyst III to form a formamide compound, wherein the catalyst III is a pincer catalyst having a structure represented by the general formula:

$$M(L)XYY' \tag{III}$$

wherein,

M is selected from Group VIIIB transition metals: Fe, Co, Ni, Ru, Rh, Pd, Os, Ir, Pt, or combinations thereof;

X, Y and Y' are independently selected from a group consisting of carbon monoxide, triphenylphosphine, pyridine, tetrahydrofuran, dimethylsulfoxide or hydrogen anion, hydroxide, chloride ion, bromide ion, iodide ion, $BH_4^-$, $BH_3CN^-$, $BH(Et)_3^-$, $BH(sec-Bu)_3^-$ or $AlH_4^-$;

L is a tridentate pincer ligand as shown in Formula IV,

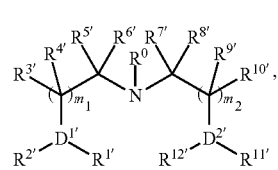

IV wherein, $m_1$ and $m_2$ are independently an integer selected from 1-3;

$D^{1'}$ and $D^{2'}$ are electron donor atoms coordinated to a metal atom, which are independently selected from a group consisting of P, N and S;

$R^0$ is selected from: a hydrogen, substituted or unsubstituted $C_1$-$C_{10}$ alkyl, substituted or unsubstituted $C_3$-$C_{10}$ cycloalkyl, substituted or unsubstituted $C_6$-$C_{24}$ aryl, substituted or unsubstituted $C_7$-$C_{25}$ arylalkyl, substituted or unsubstituted $C_4$-$C_{20}$ heteroaryl;

$R^{1'}$, $R^{2'}$, $R^{11'}$ and $R^{12'}$ are independently selected from: a hydrogen, substituted or unsubstituted $C_1$-$C_{10}$ alkyl, substituted or unsubstituted $C_3$-$C_{10}$ cycloalkyl, substituted or unsubstituted $C_4$-$C_{24}$ aryl or heteroaryl, wherein the $R^{1'}$ and $R^{2'}$, or $R^{11'}$ and $R^{12'}$ can connect to form a substituted or unsubstituted $C_3$-$C_{10}$ cycloalkyl, $C_4$-$C_{24}$ aryl or heteroalkyl;

$R^{3'}$, $R^{4'}$, $R^{5'}$, $R^{6'}$, $R^{7'}$, $R^{8'}$, $R^{9'}$ and $R^{10'}$ are independently selected from a group consisting of: a hydrogen, substituted or unsubstituted $C_1$-$C_{10}$ alkyl, $C_3$-$C_{10}$ cycloalkyl, substituted or unsubstituted $C_1$-$C_{10}$ alkoxy or $C_6$-$C_{36}$ aryl, wherein $R^{3'}$, $R^{4'}$, $R^{5'}$, $R^{6'}$, $R^{7'}$, $R^{8'}$, $R^{9'}$ and $R^{10'}$ can be connected with each other to form a substituted or unsubstituted $C_3$-$C_{10}$ aliphatic cycloalkyl, $C_4$-$C_{24}$ aryl or heteroaryl group;

wherein the "substituted" means that one or more hydrogen atoms of a group is substituted by a substitutent selected from the following group: a hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, amido.

In another preferred embodiment, the amine compound is an organic primary amine or an organic secondary amine compound.

In another preferred embodiment, the preferred $R^0$ is selected from a group consisting of H, $C_1$-$C_4$ alkyl (e.g., methyl) or phenyl.

In another preferred embodiment, the preferred $R^{1'}$, $R^{2'}$, $R^{11'}$, $R^{12'}$ are independently a phenyl, ethyl, isopropyl, t-butyl, cyclohexyl or adamantane.

In another preferred embodiment, $R^{3'}$, $R^{4'}$, $R^{5'}$, $R^{6'}$, $R^{7'}$, $R^{8'}$, $R^{9'}$, $R^{10'}$ are independently selected from a hydrogen, phenyl or pyridyl.

In another preferred embodiment, M is Ru or Ir.

In another preferred embodiment, the structure of the formamide compound is shown in formula II:

wherein, $R^1$ is selected from: a hydrogen, substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8;

$R^2$ is selected from: a substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8; wherein, $R^3$, $R^4$, $R^5$ are independently selected from: a hydrogen, substituted or unsubstituted $C_1$-$C_{20}$ alkyl, substituted or unsubstituted $C_6$-$C_{24}$ aryl, substituted or unsubstituted $C_7$-$C_{25}$ arylalkyl or heteroaryl, wherein $R^4$ and $R^5$ can connect to form a substituted or unsubstituted $C_3$-$C_{10}$ cycloalkyl, $C_4$-$C_{24}$ aryl or heteroalkyl, wherein the "substituted" means that one or more hydrogen atoms of a group is substituted by a substitutent selected from the following group: a hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, amido.

In another preferred embodiment, the formamide compounds include formamide, N, N-dimethylformamide (DMF) and N-formylmorpholine.

In the third aspect of the present invention, a tridentate pincer ligand is provided, wherein the ligand has a structure shown in the following formula:

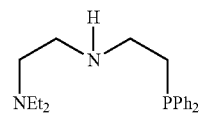

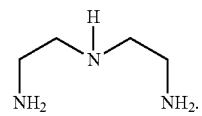

In the fourth aspect of the present invention, a catalyst is provided, wherein the catalyst comprises the ligand of the third aspect of the present invention.

In another preferred embodiment, the catalyst has the following structure:

M(L)XYY' wherein,

M is selected from Group VIIIB transition metals; Fe, Co, Ni, Ru, Rh, Pd, Os, Ir, Pt, or combinations thereof;

X, Y and Y' are independently selected from a group consisting of carbon monoxide, triphenylphosphine, pyridine, tetrahydrofuran, dimethylsulfoxide or hydrogen anion, hydroxide, chloride ion, bromide ion, iodide ions, $BH_4^-$, $BH_3CN^-$, $BH(Et)_3^-$, $BH(sec-Bu)_3^-$ or $AlH_4^-$;

L is the tridentate pincer ligand of claim 12.

In another preferred embodiment, the catalyst has the following structure:

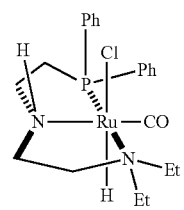

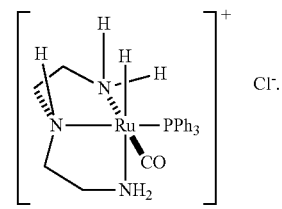

In the fifth aspect of the present invention, a use of catalyst III is provided for catalyzing the reaction of organic primary or organic secondary amine compound with carbon dioxide and hydrogen to form a formamide compound.

It should be understood that, in the present invention, each of the technical features specifically described above and below (such as those in the Examples) can be combined with each other, thereby constituting new or preferred technical solutions which need not be specified again herein.

BRIEF DESCRIPTION OF THE DRAWINGS

FIG. 1 is the X-ray single crystal diffraction pattern of ruthenium catalyst 1a.

EMBODIMENTS FOR CARRYING OUT THE INVENTION

Through long-term extensive studies and a large number of screening and testing, it has been found for the first time that an organic amine compound can react with carbon dioxide in the presence of hydrogen when catalyzed by a suitable catalyst to form formamides with high efficiency and selectivity, thus achieving the direct fixation and utilization of carbon dioxide. This formamide compound has a very wide range of applications in the industrial, pharmaceutical and materials industry, therefore, the method of the invention has a huge application prospects. The present invention is completed on this basis.

Transformation Efficiency

As used herein, term "transformation efficiency" (or efficiency) refers to the precentage of reactant consumed in the chemical reaction to the total amount of reactant initially added. The transformation efficiency of the present invention is calculated based on dimethylamine.

Number of Transformation

As used herein, the term "number of transformation" refers to the ratio of the number of moles of reactants that have been converted to the number of moles of catalyst over a period of time. The number of transformation of the present invention is calculated based on dimethylamine.

In the present invention, the transformation efficiency and the transformation number are calculated by gas chromatography or separation.

The Catalyst of the Present Invention

The pincer transition metal complex catalyst used in the present invention has the structures shown in 1a-1h, 2a-2d and 3a. Wherein the preparation of 1g, 2c-2d can be found in examples 1, 2 and 3,

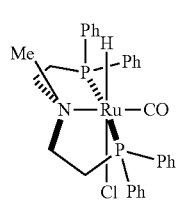

1a

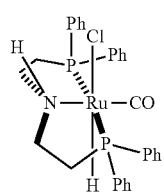

1b

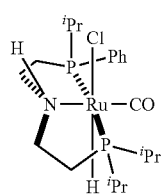

1c

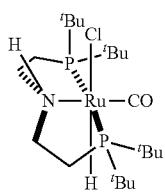

1d

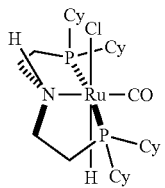

1e

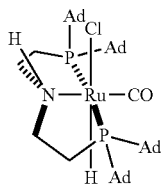

1f

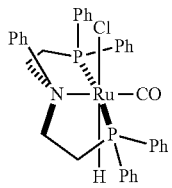

1g

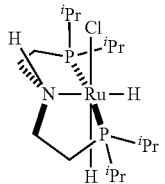

1h

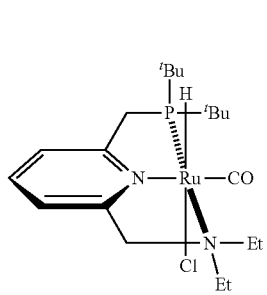

2a

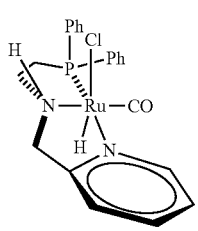

2b

-continued

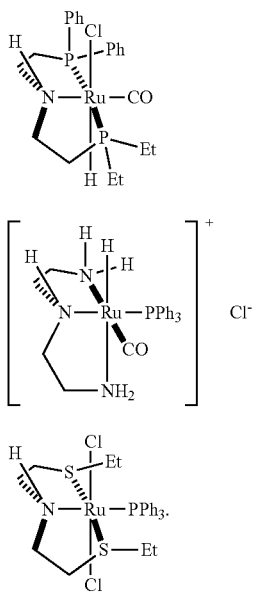

Method for Preparing Formamide Compound

The method for the preparation of formamide compound of the present invention comprises the following steps:

(A) reacting an amine compound of formula I with carbon dioxide and hydrogen under the action of catalyst III to form a formamide compound of formula II:

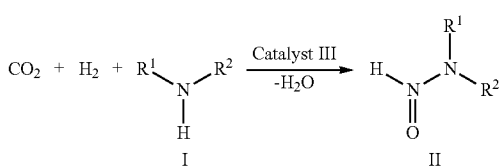

wherein, $R^1$ is selected from: a hydrogen, substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8;

$R^2$ is selected from: a substituted or unsubstituted $C_1$-$C_{20}$ alkyl, substituted or unsubstituted $C_4$-$C_{10}$ cycloalkyl, substituted or unsubstituted $C_6$-$C_{24}$ aryl, substituted or unsubstituted $C_7$-$C_{25}$ arylalkyl, —$(CH_2)_n$—$OR^3$ or —$(CH_2)_n$—$NR^4R^5$, wherein n=1-8; wherein, $R^3$, $R^4$, $R^5$ are independently selected from: a hydrogen, substituted or unsubstituted $C_1$-$C_{20}$ alkyl, substituted or unsubstituted $C_6$-$C_{24}$ aryl, substituted or unsubstituted $C_7$-$C_{25}$ arylalkyl or heteroaryl, wherein $R^4$ and $R^5$ can connect to form a substituted or unsubstituted $C_3$-$C_{10}$ cycloalkyl, $C_4$-$C_{24}$ aryl or heteroalkyl, wherein the "substituted" means that one or more hydrogen atoms of a group is substituted by a substitutent selected from the following group: a hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, amido.

The Main Advantages of the Present Invention are:

1. The invention utilizes carbon dioxide, hydrogen and organic amine compounds for the first time to react with clamp-type transition metal complex catalyst to form formamides at high efficiency. Compared with the traditional method for preparing formamides, the method of the invention realizes the high-efficiency chemical conversion and utilization of $CO_2$, and the carbon dioxide is cheap and easy to obtain, thus effectively reducing the production cost in the industrial large-scale preparation of formamide. It is a new technology which directly uses carbon dioxide as a carbon resource, thus having good application prospects.

2. The only by-product produced by the process of the present invention is water, which does not produce other wastes and meets the long-term technical objectives of environmental friendly and sustainable society.

3. The method has the advantages of user-friendly operation, mild reaction condition and low energy consumption.

4. The method uses carbon dioxide, hydrogen and dimethylamine as raw materials to prepare N, N-dimethylformamide (DMF) under moderate reaction condition, the catalytic conversion number of single-tank reaction can reach up to more than 600000; and since the catalyst used is very stable, the catalyst can be easily repeatedly recycled (more than 12 times), thus greatly improving the efficiency of the catalyst, significantly reducing the cost of the reaction.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are weight parts and weight percentage.

Example 1: Synthesis of Ruthenium Complex 1g

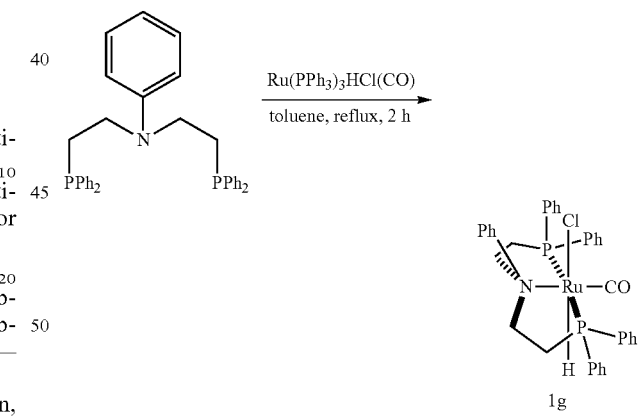

Under argon atmosphere, PhN(CH$_2$CH$_2$PPh$_2$)$_2$ (1.10 g, 2.12 mmol), toluene (20 mL) and RuHCl(CO)(PPh$_3$)$_3$ (1.90 g, 2.0 mmol) were added to a 100-mL Schlenk tube and reacted under reflux for 2 hours. After the reaction was cooled to room temperature, hexane (10 mL) was added. The precipitate was filtrated and washed with hexane, and dried in vacuo to give solid ruthenium complex 1g (1.231 g) as a white powder in 90% yield.

M.P. 178° C. 90% Yield. 1H NMR (400 MHz, CDCl$_3$) δ 8.09-7.19 (m, 25H), 4.72 (t, 2H, J=14.7 Hz), 3.54-3.36 (m, 2H), 2.19 (t, 2H, J=13.8 Hz), 1.8-1.62 (m, 2H) −13.57 (t, J=26.0 Hz, 1H) ppm. $^{31}$P NMR (161.9 MHz, CDCl$_3$) δ 51.5

(d, J=5.7 Hz) ppm. HRMS (MALDI) m/z calcd. for [C$_{35}$H$_{34}$NOP$_2$$^{96}$Ru]$^+$: 642.1186, Found: 642.1189 [M-Cl]$^+$; IR (film) 1922 cm$^{-1}$.

Example 2: Synthesis of Ruthenium Complex 2c

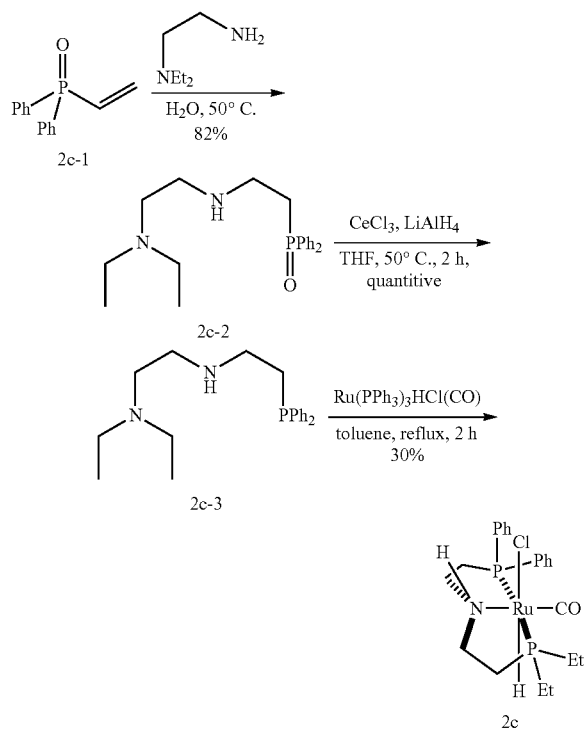

Diphenyl (vinyl) phosphine oxide (2c-1) (1.63 g, 14.0 mmol), N,N-diethylethanediamine (2.3 g, 10.0 mmol) and water (25 ml) were added to a 100 mL round bottom flask, and the mixture was stirred under 50° C. to react for 18 hours. After cooled to room temperature, the mixture was extracted with dichloromethane (25 mL×3), and dried with anhydrous sodium sulfate and filtered. The filtrate was evaporated in vacuo to remove the solvent, and the residue was separated and purified through silica gel column chromatography (eluent CH$_2$Cl$_2$:CH$_3$OH=20:1, v/v), and dried under vacuum to obtain a viscous colorless oily compound 2c-2, yield 82%.

$^1$HNMR (400 MHz, CDCl$_3$) δ7.74-7.69 (m, 4H), 7.50-7.41 (m, 6H), 2.95-2.89 (m, 2H), 2.59 (t, J=6.0 Hz, 2H), 2.53-2.42 (m, 8H), 2.00 (br s, 1H), 0.94 (t, J=7.2 Hz) ppm. $^{31}$P NMR (161.9 MHz, CDCl$_3$) δ 30.9 ppm; $^{13}$C NMR (100 MHz, CDCl$_3$) δ 132.67 (d, J$_{P-C}$=98.2 Hz), 131.57 (d, J$_{P-C}$=2.2 Hz), 130.42 (d, J$_{P-C}$=8.9 Hz), 128.46 (d, J$_{P-C}$=11.1 Hz), 52.07, 46.99, 46.76, 42.66, 30.20 (d, J$_{P-C}$=70.7 Hz), 11.48 ppm.

Under argon atmosphere, 2c-2 (2.83 g, 8.22 mmol), anhydrous cisplatin (3.04 g, 12.33 mmol) and THF (35 mL) were added to a 100-mL Schlenk tube, lithium aluminum hydride (1.25 g, 32.88 mmol) was added portionwise to the reaction system under stirring, and bubbles were released. The mixture was heated and stirred at 50° C. for 2 hours and then cooled to room temperature. The resulting suspension was added to a stirred mixture of ice-cooled brine-CH$_2$Cl$_2$ (1:2), and the solids were removed by filtration. The filtrate was stood to separate the organic phase. The aqueous phase was extracted with CH$_2$Cl$_2$ (20 mL×3). The organic phases were combined, dried over anhydrous sodium thioide and filtered. The filtrate was evaporated in vacuo to remove the solvent to give a colorless viscous liquid 2c-3, yield 100%.

$^1$H NMR (400 MHz, CDCl$_3$) δ 7.45-7.32 (m, 10H), 2.79-2.74 (m, 2H), 2.65 (t, J=6.4 Hz, 2H), 2.52-2.47 (m, 6H), 2.29 (t, J=7.6 Hz, 2H), 2.00 (br, 1H, NH), 1.00 (t, J=6.8 Hz, 6H) ppm. $^{31}$P NMR (161.9 MHz, CDCl$_3$) δ-20.40 ppm.

$^{13}$C NMR (100 MHz, CDCl$_3$) δ 138.64, 138.52, 132.72, 132.54, 128.45, 128.38, 128.32, 52.62, 47.40, 47.02, 46.90, 46.68, 29.18, 29.06, 11.92. ppm.

Under argon atmosphere, 2c-3 (659 mg, 2.0 mmol), toluene (20 mL) and RuHCl(CO)(PPh$_3$)$_3$ (1.59 g, 1.67 mmol) were added to a 100-mL Schlenk tube and heated to reflux for 2 hours. After the reaction mixture was cooled to room temperature, hexane (10 mL) was added to precipitate a white precipitate, which was filterated and washed with a small amount of hexane, dried in vacuo to give ruthenium complex 1g (285 mg) as a white solid in 30% yield.

M.P. 200° C.; 1H NMR (400 MHz, CDCl$_3$) δ 7.72-7.25 (m, 10H), 4.53 (s, 1H), 3.63-3.39 (m, 3H), 3.24-3.20 (m, 1H), 3.13-3.11 (m, 1H), 2.97-2.92 (m, 3H), 2.78-2.67 (m, 2H), 2.55 (br, 1H), 2.23 (t, J=14.4 Hz, 1H), 1.20 (t, J=5.6 Hz, 3H), 1.11 (t, J=6.4 Hz, 3H), -16.2 (d, J=28 Hz, 1H) ppm;

$^{31}$P NMR (161.9 MHz, CDCl$_3$) δ 71.5 (d, J=23.2 Hz) ppm; HRMS (MALDI) m/z calcd. for [C$_{21}$H$_{30}$N$_2$OP$^{96}$Ru]$^+$: 453.1166, Found: 453.1167 [M-Cl]$^+$; IR (film) 1976, 1908, 1891 cm$^{-1}$.

Example 3: Synthesis of Ruthenium Complex 2d

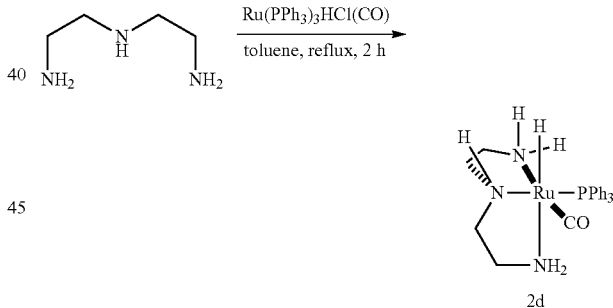

Under argon atmosphere, HN(CH$_2$CH$_2$NH$_2$)$_2$ (62 mg, 0.6 mmol), toluene (10 mL) and RuHCl(CO)(PPh$_3$)$_3$ (475 mg, 0.5 mmol) were added to a 100-mL Schlenk tube and reacted under reflux for 2 hours. After the reaction mixture was cooled to room temperature, hexane (10 mL) was added. The obtained white precipitate was filterated and washed with hexane, dried in vacuo to give ruthenium complex 2d (0.256 g) as a white solid in 96% yield.

$^1$H NMR (400 MHz, CDCl$_3$) δ 7.54-7.44 (m, 15H), 5.31 (br, 2H), 5.05 (br, 1H), 3.38 (s, 1H), 3.17 (s, 2H), 3.98-2.85 (m, 2H), 2.62 (s, 1H), 2.30 (s, 1H), 1.86-1.79 (m, 2H), -12.7 (d, J=25.2, 1H) ppm.

$^{31}$P NMR (161.9 MHz, CDCl$_3$) δ 67.9 ppm.

HRMS (MALDI) m/z calcd. for [C$_{23}$H$_{29}$N$_3$OP$^{96}$Ru]$^+$: 490.1119, Found: 490.1117 [M-Cl]$^+$. IR (film) 1918 cm$^{-1}$.

Example 4: Influence of Different Temperature on Morpholine Formylation Reaction Catalyzed by Ruthenium Complex

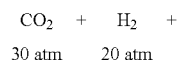

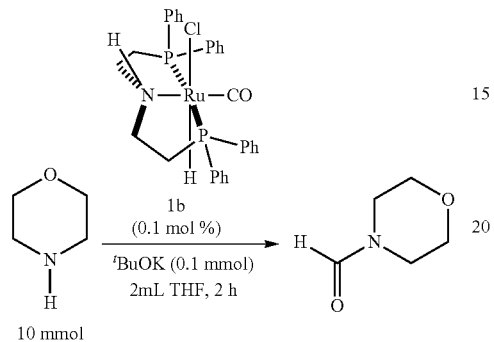

Ruthenium complex 1b (6.1 mg, 0.01 mmol), potassium tert-butoxide (1.1 mg, 0.01 mmol), tetrahydrofuran (2 ml) and morpholine (872 mg, 10 mmol) were added to a 125-mL Parr autoclave under a nitrogen atmosphere in a glove box. The autoclave was sealed and taken out from the glove box, the carbon dioxide was added at 30 atm, and then hydrogen was added at 20 atm to total pressure 50 atm. The mixture in reactor was heated and stirred in an oil bath at the setting temperature for 2 hours, and then the reactor was cooled to room temperature in a water bath, and the remaining gas was slowly released in a fume hood. p-xylene internal standard (50 μL) was added into the mixture and the yield of N-formylmorpholine was determined by gas chromatography (see Table 1 for results).

Agilent 6890 gas chromatograph, DM-Wax column (60 m×0.32 mm×1 μm). GC conditions: DM-wax column, carrier gas: $N_2$, Injection temp.: 250° C., Detector temp.: 3000° C., flow rate: 1 mL/min, oven temp.: 40° C., 1 min, 10° C./min, 230° C., 30 min.

TABLE 1

Effect of Different Temperature on Morpholine Formylation Reaction Catalyzed by Ruthenium Complex 1b

| Temperature (° C.) | 60 | 80 | 100 | 110 | 120 | 130 | 140 |
|---|---|---|---|---|---|---|---|
| Yield (%) | 4 | 23 | 36 | 59 | 61 | 58 | 49 |

In the above table: the yield of N-methylmorpholine is determined by gas chromatography with p-xylene as internal standard.

As can be seen from Table 1, the change of temperature has a significant effect on the reaction results. The reaction can hardly proceed below 60° C., while the yield of the product reduced when the temperature is over 140° C. Therefore, the temperature in the reaction was between 110° C. to 130° C., preferably 120° C.

Example 5: Influence of Different Solvents on Morpholine Formylation Reaction Catalyzed by Ruthenium Complex 1b

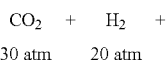

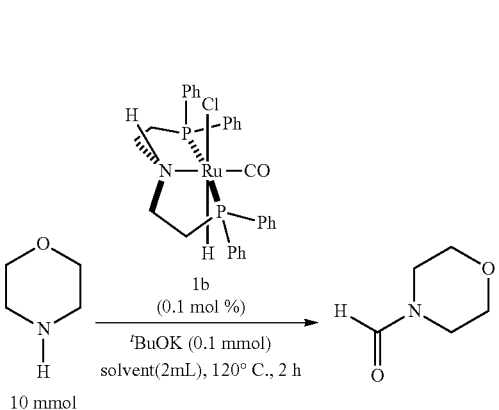

Steps similar to those in example 4 were employed, and ruthenium complex 1b was used as catalyst. At 120° C. and in the presence of $CO_2$ and $H_2$ at 30 atm and 20 atm, respectively, morpholine was stirred for 2 hours in different solvents in a reactor. The yield of N-formylmorpholine was determined by gas hromatography. The results are shown in table 2:

TABLE 2

Influence of Different Solvents on Morpholine Formylation Reaction Catalyzed by Ruthenium Complex

| Solvent | tetrahydrofuran | acetonitrile | toluene | methanol | solvent-free |
|---|---|---|---|---|---|
| Yield (%) | 58 | 54 | 44 | 58 | 1 |

In the above table: the yield of N-methylmorpholine is determined by gas chromatography with p-xylene as internal standard.

As can be seen from Table 2, the reaction solvents have a significant influence on the yield of the product. In a polar solvent such as acetonitrile, methanol or THF, the product yield is from medium to good, while the yield in toluene is slightly lower, and no reaction occurs when solvent-free. Therefore, THF or methanol was used as the reaction solvent in further condition selection.

Example 6: Influence of Pressure of CO$_2$ and H$_2$ on Morpholine Formylation Reaction Catalyzed by Ruthenium Complex 1b

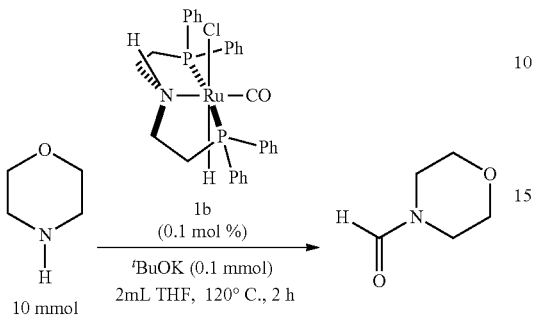

Steps similar to those in example 4 were employed, and ruthenium complex 1b (0.01 mmol) was used as catalyst. Under different CO$_2$ and H$_2$ partial pressure, morpholine formylation reaction was catalyzed for 2 hours at 120° C. The reaction results are shown in table 3:

TABLE 3

Influence of pressure of CO$_2$ and H$_2$ on Morpholine Formylation Reaction Catalyzed by Ruthenium Complex 1b

| CO$_2$ pressure (atm) | 10 | 20 | 30 | 35 | 40 | 20 | 50 | 10 |
|---|---|---|---|---|---|---|---|---|
| H$_2$ pressure (atm) | 10 | 20 | 30 | 35 | 20 | 40 | 10 | 50 |
| GC yield (%) | 18 | 49 | 59 | 75 | 61 | 50 | 51 | 55 |

In the above table: the yield of N-methylmorpholine is determined by gas chromatography with p-xylene as internal standard.

It can be seen from table 3 that the change of CO$_2$ and H$_2$ pressure has great influence on the reaction results. Under the pressure conditions shown in the table, the greatest catalyzing effect was achieved by 1b when both of CO$_2$ and H$_2$ are at 35 atm, in which the yield of N-Formylmorpholine can reach up to 75%.

Example 7: Screening of Catalysts (1a-1h, 2a-2d, 3a) in Morpholine Formylation Reaction

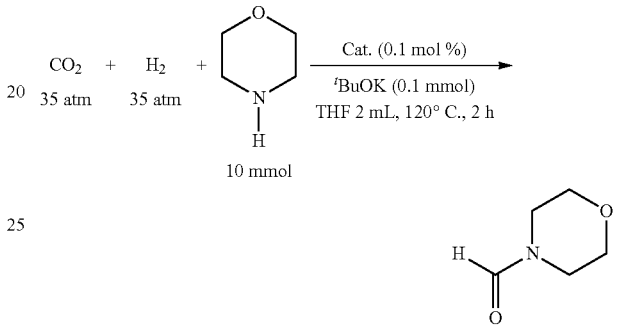

Steps similar to those in example 4 were employed, and 0.1 mol % of ruthenium complexes 1a-1h, 2a-2d, 3a were used as catalyst, respectively. At 120° C., morpholine (10 mmol), CO$_2$ (35 atm) and H$_2$ (35 atm) were reacted in THF solvent for 2 hours, and the results are shown in table 4:

TABLE 4

Influence of catalysts 1a-1h, 2a-2d, 3a on morpholine formylation reaction

| Catalyst | 1a | 1b | 1c | 1d |
|---|---|---|---|---|
| Yield (%) | 79 | 75 | 68 | 78 |

| Catalyst | 1e | 1f | 1g | 1h |
|---|---|---|---|---|
| Yield (%) | 72 | 68 | 36 | 72 |

TABLE 4-continued

Influence of catalysts 1a-1h, 2a-2d, 3a on morpholine formylation reaction

| Catalyst | 2a | 2b | 2c | 2d |
|---|---|---|---|---|
| Yield (%) | 64 | 35 | 36 | 2 |

| Catalyst | 3a |
|---|---|
| Yield (%) | 8 |

In the above table: the yield of N-methylmorpholine is determined by gas chromatography with p-xylene as internal standard.

It can be seen from Table 4 that for the PNP tridentate pincer metal catalysts 1a-1h, 2a-2d, 3a, PNP tridentate ligand complexes 1a-1h can more efficiently catalyze morpholine formylation reaction than PNN and SNS tridentate ligand complexes (2a-2c, 3a) under the same reaction conditions. Therefore, the preferred catalyst is PNP-type tridentate ligand complex, more preferably a pincer tridentate ligand ruthenium complex 1a.

Example 8: Influence of Different Amounts of Alkali on Morpholine Formylation Reaction Catalyzed by Ruthenium Complex 1b

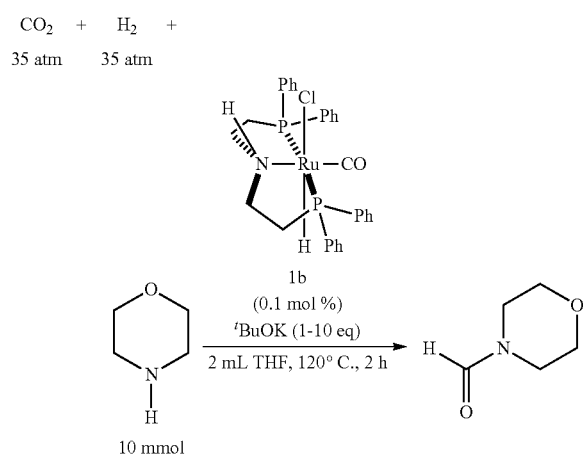

Steps similar to those in example 4 were employed, while ruthenium complex 1b was used as catalyst, and different amounts of potassium tert-butoxide as basic additive. Morpholine (20 mmol) and $CO_2$ (35 atm) and $H_2$ (35 atm) were reacted at 120° C. in THF solvent for 2 hours. The reaction results are shown in table 5:

TABLE 5

Influence of Different Alkali Amount on Morpholine Formylation Reaction Catalyzed by Ruthenium Complex 1b

| $^t$BuOK (equiv) | 0 | 1 | 5 |
|---|---|---|---|
| yield (%) | 72 | 73 | 70 |

In the above table: the yield of N-methylmorpholine is determined by gas chromatography with p-xylene as internal standard.

As can be seen from Table 5, the amount of base (potassium t-butoxide) used in this reaction did not significantly affect the catalytic effect. Since the reaction substrate morpholino itself is a organic base with strong basicity, there is no need to add additional base to activate ruthenium complex 1b, therefore, in subsequent preferred embodiment, alkali other than amine substrate was not added.

Example 9: Morpholine Formylation Catalyzed by Using 1/10000 of Molar Equivalent of Ruthenium Complex 1a

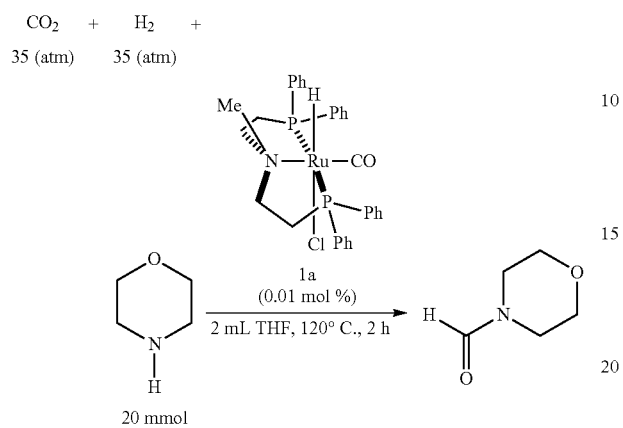

Under a nitrogen atmosphere, Ruthenium complex 1a (1.2 mg, 0.002 mmol), tetrahydrofuran (2 ml) and morpholine (1.742 g, 20 mmol) were added to a 125-mL Parr autoclave in a glove box. The autoclave was sealed and taken out from the glove box, carbon dioxide was added to 35 atm, and then hydrogen was added at 35 atm, and the total pressure was stably maintained at 60 atm. The mixture in reactor was heated and stirred to react in an oil bath at 120° C. for 2 hours and then the reactor was cooled to room temperature in a water bath, and the remaining gas was slowly released in a fume hood. P-xylene (50 μL) was added as internal standard, and the yield of N-formylmorpholine was determined by gas chromatography (92%).

Example 10: Morpholine Formylation Catalyzed by Using Different Amounts of Ruthenium Complex 1a Steps similar to those of Example 9 were employed, the molar amount of the catalyst was reduced to one of twenty thousandths, of forty thousandth and of hundred thousandths, respectively. And the reaction was performed with morpholine (20 mmol) at 120° C. for 2 hours under $CO_2$ and $H_2$ pressure 35 atmospheres, respectively. The results are shown in Table 6.

TABLE 6

Morpholine Formylation Reaction Catalyzed by using Different amounts of ruthenium complex 1b

| The amount of catalyst 1a (mol %) | 0.005 | 0.0025 | 0.001 |
|---|---|---|---|
| Yield (%) | 99 | 69 | 61 |
| TOF ($h^{-1}$) | 10000 | 13870 | 30500 |

In the above table, the yield of N-methylmorpholine is determined by gas chromatography with p-xylene as internal standard.

As can be seen from Table 6, the catalytic efficiency of the catalyst 1a can be advantageously improved by lowering the amount of the catalyst.

Example 11: Morpholine Formylation Catalyzed by Using 1/2000000 of Molar Amount of Ruthenium Complex 1a

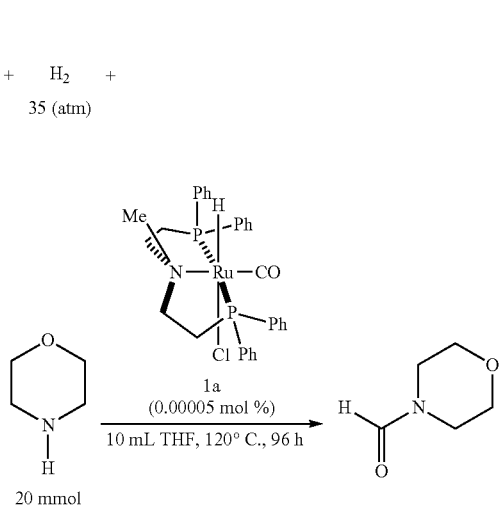

Under a nitrogen atmosphere in a glove box, 6.1 mg of the ruthenium complex 1a was dissolved in 10 mL of tetrahydrofuran and stirred to form a catalyst 1a stock solution. 0.1 ml of the above solution was added to a 125-mL Parr autoclave (0.06 mg, 0.0001 mmol 1a), and tetrahydrofuran (10 mL), morpholine (17.31 g, 200 mmol) was added successively. The autoclave was sealed and taken out from the glove box, followed by the addition of carbon dioxide and hydrogen at 35 atm separately. The reaction system was heated and stirred in an oil bath at 120° C. for 42 hours and then the autoclave was cooled to room temperature in a water bath, and then the remaining gas was slowly released in a fume hood. The $CO_2$ and hydrogen were charged again at 35 atm and then heated at 120° C. for 32 hours. The autoclave was cooled in a water bath to room temperature and the remaining gas was slowly released in the fume hood. 35 atm of carbon dioxide and hydrogen was filled again, and heated at 120° C. for 22 hours, and the autoclave pressure is no longer reduced. After the reaction system was cooled to room temperature, the residual gas was slowly released to obtain a pale yellow liquid. The liquid was filtered through a short column of silica gel (2 cm) and washed with ethyl acetate. The resulting filtrate was dried over anhydrous sodium sulfate, filtered and the solvent was evaporated in vacuo and vacuum-dried to give N-formylmorpholine (22.447 g) in 97% yield.

$^1$H NMR (400 MHz, CDCl$_3$) δ 8.06 (s, 1H), 3.71 (t, J=4.8 Hz, 2H), 3.67 (t, J=4.8 Hz, 2H), 3.58 (t, J=4.8 Hz, 2H), 3.41 (t, J=4.8 Hz, 2H) ppm.

Example 12: Morpholine Formylation Catalyzed by Using 1/2500000 Molar Amount of Ruthenium Complex 1a

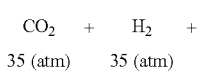

-continued

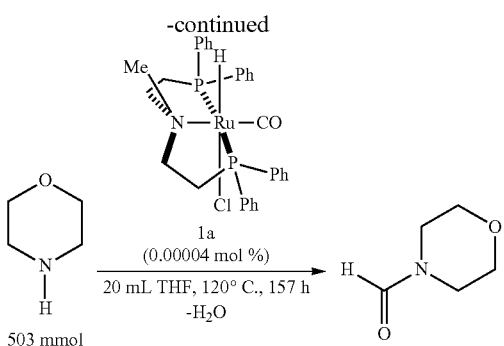

Under a nitrogen atmosphere in a glove box, 6.1 mg of the ruthenium complex 1a was dissolved in 10 mL of tetrahydrofuran, 0.2 ml (0.12 mg, 0.0002 mmol) of the above solution was added to a 300-mL Parr autoclave, and 20 mL tetrahydrofuran, morpholine (43.80 g, 502.8 mmol) was added successively. The autoclave was sealed and taken out from the glove box, and carbon dioxide and hydrogen were filled at 35 atm separately. After 5 minutes, the total pressure was stably maintained at 60 atm. The reaction system was heated in an oil bath at 120° C., while the pressure was raised to 110 atm and stirred for 46 hours, and then the pressure was reduced to 60 atm. The reaction system was cooled to room temperature in a water bath, and then the remaining gas was slowly released in a fume hood. Then the system was recharged with carbon dioxide and hydrogen at 35 atm respectively and reheated to 120° C. After stirred for 51 hours, the mixture was allowed to cool to room temperature, vented and then refilled with carbon dioxide and hydrogen at 35 atm respectively. This process was repeated for four times, in which the time used was 46, 51, 24 and 36 hours. The autoclave was then allowed to cool to room temperature in a water bath and the remaining gas was slowly released in a fume hood to give a pale yellow liquid. The liquid was filtered through a 2 cm silica gel short column and washed with ethyl acetate. The resulting solution was dried over anhydrous sodium sulfate, filtered and the filterate was evaporated in vacuo to remove solvent and vacuum-dried to give N-formylmorpholine (42.63 g) in 74% yield.

Example 13: Morpholine Formylation Catalyzed by Using 1/4000000 of Molar Equivalent of Ruthenium Complex 1a

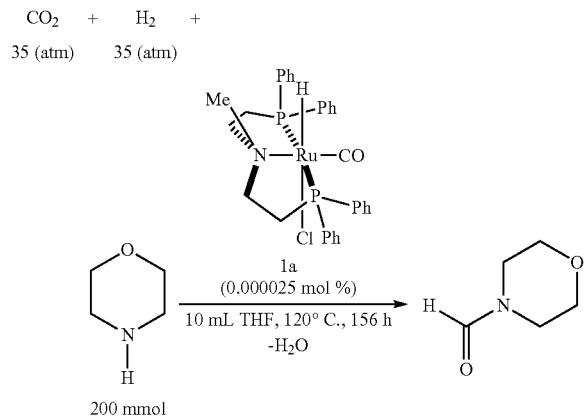

Under a nitrogen atmosphere a the glove box, 6.1 mg of the ruthenium complex 1a was dissolved in 10 mL of tetrahydrofuran, 50 μL (0.03 mg, 0.00005 mmol) of the above solution was added to a 300-mL Parr autoclave, and 10 mL tetrahydrofuran, morpholine (17.32 g, 200 mmol) was added successively. The autoclave was sealed and taken out from the glove box, the carbon dioxide and hydrogen were filled at 35 atm separately. The total pressure was stably maintained at 60 atm. The reaction mixture was heated and stirred in an oil bath at 120° C. for 156 hours and then the pressure stopped to reduce. After cooled to room temperature in water bath, the residual gas was slowly released to obtain a mixture of pale yellow liquid and white solid. The mixture was filtered through a 2 cm silica gel column and washed with ethyl acetate. The resulting solution was dried over anhydrous sodium sulfate and evaporated in vacuo to remove solvent, and vacuum-dried to give 4.71 g colourless liquid in 20% yield.

Example 14: Morpholine Formylation Catalyzed by Using 1/1000000 of Molar Amount of Ruthenium Complex 1b

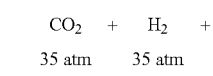

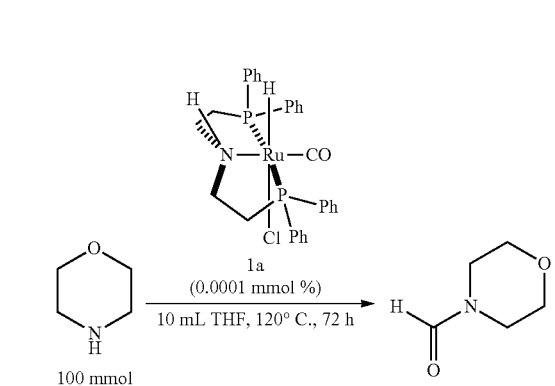

Under a nitrogen atmosphere in the glove box, 6.1 mg of the ruthenium complex 1b was dissolved in 10 mL of tetrahydrofuran, 0.1 ml of the above solution was added to a 600-mL Parr autoclave, and 10 mL THF and morpholine (8.720 g, 200 mmol) was added successively. The autoclave was sealed and taken out from the glove box, followed by the addition of carbon dioxide and hydrogen at 35 atm separately. The total pressure was set at 60 atm. The reaction system was heated and stirred in an oil bath at 120° C. for 72 hours and then cooled to room temperature in a water bath, and then the remaining gas was slowly released in a fume hood to obtain colorless liquid. P-xylene (500 μL) was added as internal standard, and the yield of N-formylmorpholine was determined by gas chromatography (97%).

The resulting solution was filtered through a 2 cm silica gel column and washed with ethyl acetate and dried over anhydrous sodium sulphate. The solvent was removed by rotary evaporation to give pale yellow liquid N-formylmorpholine (10.701 g) in a yield of 93%.

Example 15: Effect of Different Temperature on DMF Synthesis Catalyzed by Ruthenium Complex 1a

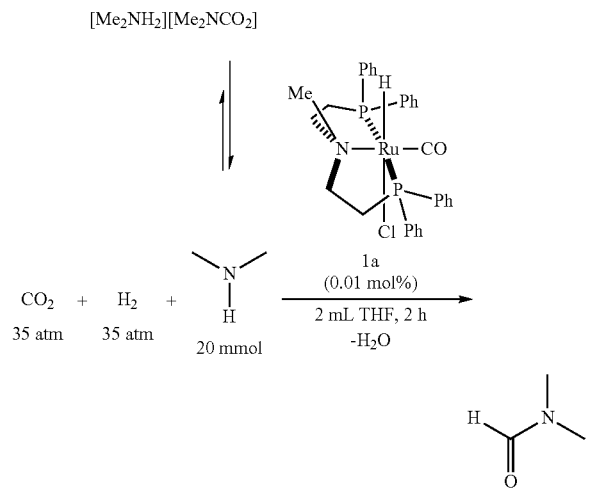

Under a nitrogen atmosphere in the glove box, ruthenium complex 1a (1.2 mg, 0.002 mmol), THF (2 mL) and the equivalent reactant of dimethylamine, i.e., dimethylamine carbon dioxide salt (1.350 g, 20 mmol dimethylamine) were added successively. The autoclave was sealed and taken out from the glove box, carbon dioxide and hydrogen were added at 35 atm separately, the total pressure was stably maintained at about 60 atm. The mixture in reactor was heated and stirred in an oil bath at the setting temperature for 2 hours, and then the reactor was cooled to room temperature in a water bath, and the remaining gas was slowly released in a fume hood. P-xylene internal standard (50 μL) was added into the mixture and the yield of DMF was determined by gas chromatography.

Agilent 6890 gas chromatograph, DM-Wax column (60 m×0.32 mm×1 μm). GC conditions: DM-wax column, carrier gas: $N_2$, Injection temp.: 250° C., Detector temp.: 300° C., flow rate: 1 mL/min, oven temp.: 40° C., 1 min, 10° C./min, 230° C., 30 min. The reaction results are shown in table 7.

TABLE 7

Effect of Different Temperature on dimethylamine Formylation Reaction Catalyzed by Ruthenium Complex 1a

| Temperature (° C.) | 60 | 80 | 90 | 100 | 110 | 120 |
|---|---|---|---|---|---|---|
| yield (%) | 7 | 18 | 30 | 38 | 57 | 53 |

In the above table, the yield of DMF is determined by gas chromatography with p-xylene as internal standard.

As can be seen from Table 7, the changes in temperature have a significant effect on the reaction results. The reaction can hardly proceed under 60° C., while the yield of the product reduced when the temperature is over 120° C. Therefore, the temperatures in the preferred embodiments were between 110° C. to 120° C., preferably at 110° C.

Example 16: Influence of Pressure of $CO_2$ and $H_2$ on Synthesis of DMF from Dimethylamine Formylation Catalyzed by Ruthenium Complex 1a

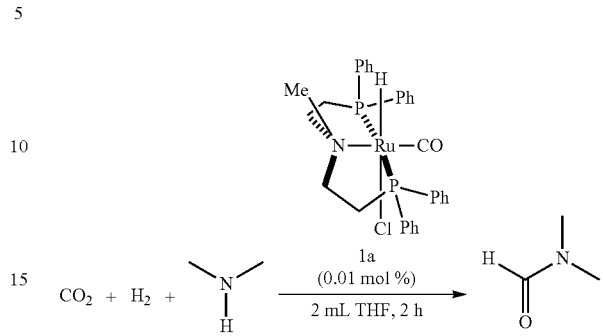

Steps similar to those in example 15 were employed, ruthenium complex 1a (0.01 mmol) was used as catalyst, the dimethylamine carbon dioxide salt (1.350 g, 20 mmol) was used as the precursor of dimethylamine, and under different $CO_2$ and $H_2$ partial pressure, the reaction was performed for 2 hours at 1100. The reaction results are shown in table 8:

TABLE 8

Influence of pressure of $CO_2$ and $H_2$ on Synthesis of DMF from dimethylamine Formylation Catalyzed by Ruthenium Complex 1a

| $CO_2/H_2$ (atm/atm) | 10/10 | 15/15 | 20/20 | 25/25 | 30/30 | 35/35 | 5/65 |
|---|---|---|---|---|---|---|---|
| DMF yield (%) | 13 | 16 | 36 | 40 | 46 | 59 | 27 |
| $CO_2/H_2$ (atm/atm) | 10/60 | 15/55 | 20/50 | 30/40 | 40/30 | 50/20 | 60/10 |
| DMF yield (%) | 35 | 41 | 39 | 46 | 53 | 18 | 1 |

In the above table, the yield of DMF is determined by gas chromatography with p-xylene as internal standard.

It can be seen from table 8 that the changes in $CO_2$ and $H_2$ pressure have large influence on the reaction results. Within the pressure conditions in the table, both of the best pressure of $CO_2$ and $H_2$ are 35 atm, in which the yield of DMF can reach up to 59%.

Example 17: Dimethylamine Formylation Reaction Catalyzed by 1/10000 of Molar Equivalent of Ruthenium Complex 1a

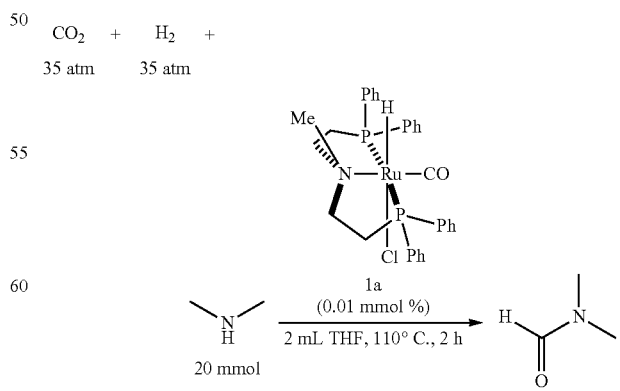

Steps similar to those of Example 15 were employed, while the morpholine was replaced with dimethylamine carbon dioxide salt (1.342 g, 20 mmol), and the reaction was performed at 110° C., under $CO_2$ and $H_2$ of 35 atm for 2 hours.

p-xylene (50 μL) was added into the reaction system as internal standard and the yield DMF was determined to be 84% by gas chromatography. The resulting solution was filtered through 2 cm silica gel column, and the solution obtained after washed with ethyl acetate was dried over anhydrous sodium sulphate. The solvent was removed by rotary evaporation to give colorless liquid DMF in 59% yield.

$^1$H NMR (400 MHz, CDCl3) δ 8.02 (s, 1H), 2.96 (s, 3H), 2.89 (s, 3H) ppm.

Example 18: Dimethylamine Formylation Reaction Catalyzed by Using 1/50000 of Molar Equivalent of Ruthenium Complex 1a

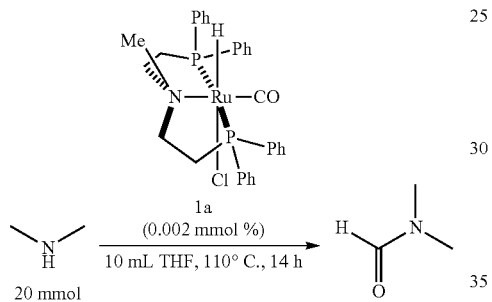

Under a nitrogen atmosphere in a glove box, ruthenium complex 1a (1.2 mg, 0.002 mmol), THF (10 mL) and dimethylamine carbon dioxide salt (6.710 g, 100 mmol dimethylamine) were added successively. The autoclave was sealed and taken out from the glove box, followed by the addition of carbon dioxide at 35 atm and hydrogen at 35 atm. The reaction system was heated and stirred in a 110° C. oil bath for 14 hours. The reactor was cooled to room temperature in a water bath, and then the remaining gas was slowly released in a fume hood to obtain colorless liquid. The yield DMF was determined to be 89% by gas chromatography with 50 μL p-xylene as internal standard.

The resulting colorless transparent liquid was distilled under reduced pressure (80° C., 3.1 torr) to give 6.89 g colorless liquid, i.e., aqueous DMF ($^1$H NMR analysis showed that the water content was usually between 7% to 16%, and the yield was calculated by 20%), the yield was 76%.

Example 19: Dimethylamine Formylation Reaction Catalyzed by Using 1/270000 of Molar Equivalent of Ruthenium Complex 1b

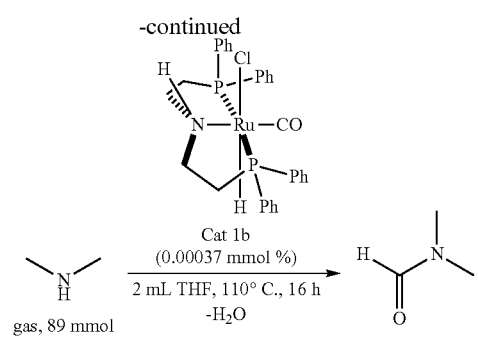

Under a nitrogen atmosphere in a glove box, Ruthenium complex 1b (0.2 mg, 0.00033 mmol) and 2 mL tetrahydrofuran were added successively to a 125-mL Parr autoclave. The autoclave was sealed and taken out from the glove box, and was filled with dimethylamine gas (about 4.0 g, 89 mmol) in dry ice bath. The autoclave was naturally heated to room temperature, followed by the addition of carbon dioxide and hydrogen at 35 atm separately. The reactor was heated and stirred in an oil bath at 110° C. for 16 hours. The autoclave was cooled to room temperature in a water bath, and then the remaining gas was slowly released in a fume hood. The yield of DMF was determined to be 46% by gas chromatography with p-xylene (50 μL) added into the mixture as internal standard.

Example 20: Dimethylamine Formylation Reaction Catalyzed by Using 1/260000 Ruthenium Complex 1b

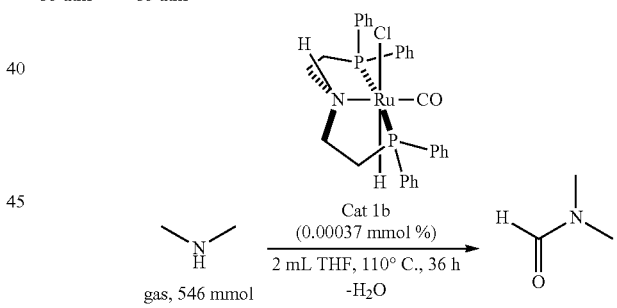

Under a nitrogen atmosphere in a glove box, Ruthenium complex 1b (1.2 mg, 0.002 mmol) and tetrahydrofuran (2 mL) were added to a 300-mL Parr autoclave. The autoclave was sealed and taken out from the glove box, and was filled with dimethylamine gas (6.8 g, 151 mmol) in dry ice bath. After naturally warmed to room temperature, carbon dioxide and hydrogen were added at 35 atm separately, and the total pressure was stably maintained at about 60 atm. The reactor was placed in an oil bath at 120° C. for 16 hours and cooled to room temperature, and then the remaining gas was slowly released in a fume hood. The reactor was refilled with dimethylamine gas (7.8 g, 173 mmol) in dry ice bath, naturally cooled to room temperature, followed by adding carbon dioxide and hydrogen at 35 atm separately. The reactor was heated and stirred in an oil bath at 110° C. for 4 hours, and the system pressure was reduced to 58 atm. The autoclave was cooled to room temperature in a water bath and the remaining gas was carefully released. And then carbon dioxide and hydrogen at 35 atm separately were refilled with and stirred to react in oil bath for 14 hours, the pressure was reduced to 60 atm. The reactor was cooled to room temperature in a water bath, and then the remaining gas was slowly released in a fume hood. Dimethylamine gas (10 g, 222 mmol) was refilled in a dry ice bath, and then carbon dioxide and hydrogen at 35 atm were successively refilled, the reactor was heated and stirred in an oil bath at 110° C. for 6.5 hours, cooled to room temperature in a water bath and the remaining gas was released. Carbon dioxide and hydrogen at 35 atm were separately refilled, stirred and heated in an oil bath at 110° C. for 5 hours, and the pressure was reduced to 70 atm. The reaction system was then allowed to cool to room temperature in a water bath and the remaining gas was slowly released in a fume hood to give faint yellow liquid. colorless liquid DMF (27.48 g, $^1$H NMR analysis showed that the water content was usually between 7% to 16%, and the yield was calculated by 20%) was obtained by distillation under reduced pressure (80° C., 3.1 torr) with a yield of 64%.

Example 21: Dimethylamine Formylation Reaction Catalyzed by Using 1/720000 of Molar Equivalent of Ruthenium Complex 1b

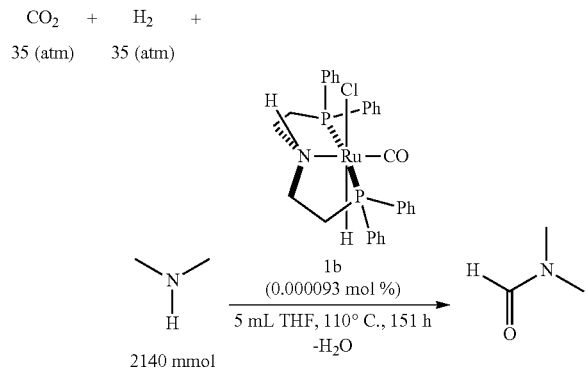

Under a nitrogen atmosphere in a glove box, Ruthenium complex 1b (1.2 mg, 0.002 mmol) and 5 mL tetrahydrofuran were added to a 600-mL Parr autoclave. The autoclave was sealed and taken out from the glove box, and was filled with dimethylamine gas (34.0 g, 755 mmol) in a dry ice bath. Naturally heated to room temperature, and 35 atm carbon dioxide and 35 atm hydrogen were successively filled. After stirred and heated for 41 hours in a 110° C. oil bath, the pressure was reduced to 55 atmospheres. The reaction system was cooled to room temperature in a water bath, and then the remaining gas was slowly released in a fume hood. The reactor was refilled with dimethylamine gas (62.4 g, 1387 mmol) in a dry ice bath. The reactor was naturally heated to room temperature, and charged with 35 atm carbon dioxide and hydrogen at 35 atm. The reactor was heated for 41 hours in a 110° C. oil bath, the pressure was reduced to 65 atmospheres, then the autoclave is again cooled in water bath to room temperature, the remaining gas was slowly released in a fume hood, and then 35 atm carbon dioxide and hydrogen at 35 atm were refilled. The reactor was heated and stirred in an oil bath at 110° C. for 69 hours, and the system pressure was reduced to 73 atm. The reactor was cooled to room temperature in a water bath, and then the remaining gas was slowly released in a fume hood to obtain faint yellow liquid. After recovering 62.0 g dimethylamine carbonate having a boiling point of 60-63° C. (comprises water and 5 ml of THF), the second fraction DMF (109.03 g, $^1$H NMR analysis showed that the water content was usually between 7% to 16%, and the yield was calculated by 20%) was obtained by distillation under reduced pressure (80° C., 3.1 torr) with a yield of 56%.

Example 22: Dimethylamine Formylation Reaction Catalyzed by Using 1/50000 of Molar Equivalent of Ruthenium Complex 1b and the Recycle of Catalyst 1b

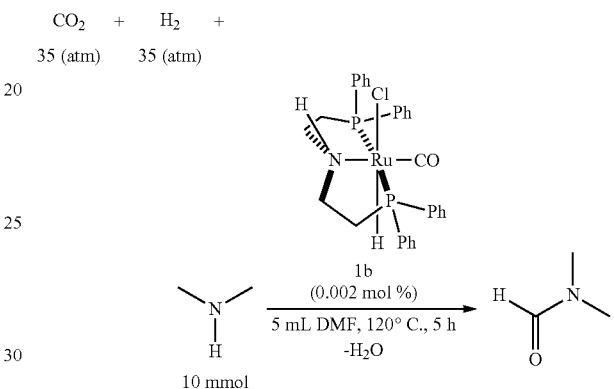

Under an air atmosphere, ruthenium complex 1b (6.0 mg, 0.01 mmol), 5 mL of DMF and freshly prepared dimethylamine carbonate (abbreviated as: DIMCARB, comprising dimethylamine in a molar ratio of 2:1 to $CO_2$, 35.2 g, 525 mmol dimethylamine). The air in the autoclave was replaced with carbon dioxide for three times, and then carbon dioxide and hydrogen were charged at 35 atm respectively, and the pressure was stably maintained at about 60 atm. After heated for 2.5 hours in a 120° C. oil bath, the pressure was reduced to 58 atmospheres. The autoclave was cooled to room temperature in a water bath to release the remaining gas in a fume hood, and then carbon dioxide and hydrogen was refilled at 35 atm respectively. The reactor was heated and stirred in an oil bath at 120° C. for another 2.5 hours, and the system pressure was reduced to 64 atm. The reactor was cooled to room temperature in a water bath, and then the remaining gas was slowly released in a fume hood to obtain faint yellow liquid. The obtained liquid was moved to a round bottom flask, distilled under reduced pressure (80° C., 3.1 torr) to give 33.74 g of a colorless liquid mixture of DMF and water ($^1$H NMR analysis showed that the water content was usually between 7% to 16%, and the yield was calculated according to the water content of 20%). The remaining small amount of liquid in the round bottom flask was diluted with 5 ml of DMF and transferred to a 300 mL Parr autoclave again, then about 35 g of dimethylamine carbonate was added and the above procedure was repeated for the next round of dimethylformamide reaction. After the dimethylformylation reaction was cycled for 12 times, the catalytic effect was still well maintained (see Table 9).

TABLE 9

| Recycling of catalyst 1b in dimethylformylation reaction | | | | | | | | | | | | |
|---|---|---|---|---|---|---|---|---|---|---|---|---|
| Cycle (time) | 1 | 2 | 3 | 4 | 5 | 6 | 7 | 8 | 9 | 10 | 11 | 12 |
| DIMCARB (g) | 35.2 | 38.2 | 33.2 | 34.3 | 33.8 | 33.8 | 39.6 | 34.1 | 35.6 | 33.9 | 35.1 | 34.6 |
| Yield (%) | 71 | 44 | 67 | 55 | 44 | 52 | 47 | 58 | 63 | 60 | 51 | 56 |
| TON | 37000 | 25000 | 33300 | 27920 | 22400 | 25900 | 24300 | 29740 | 33680 | 30000 | 26750 | 28870 |
| TOF ($h^{-1}$) | 6160 | 5000 | 6660 | 5580 | 4480 | 5150 | 4860 | 4200 | 5610 | 5000 | 4860 | 5770 |

The above table shows the yield of DMF obtained by distillation under reduced pressure (80° C., 3.1 torr).

Example 23: Morpholine Formylation Reaction Catalyzed by Using One of Thousand of Molar Equivalent of Iridium Complex 1h

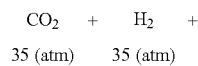

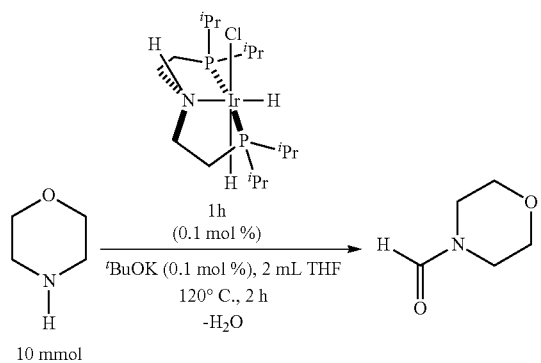

Ruthenium complex 1h (5.0 mg, 0.01 mmol), 2 mL of tetrahydrofuran, potassium tert-butoxide (1.1 mg, 0.01 mmol) and morpholine (872 mg, 10 mmol) were added to a 125-mL Parr autoclave in a glove box fulfilled with nitrogen. The autoclave was sealed and taken out from the glove box, followed by the addition of carbon dioxide and hydrogen at 35 atm separately. After a few minutes, the total pressure was stably maintained at about 60 atm. The reactor was heated and stirred in an oil bath at 120° C. for 2 hours and then cooled to room temperature in a water bath, and then the remaining gas was slowly released in a fume hood. The yield of reaction was determined to be 71% by gas chromatography with p-xylene (50 μL) added as internal standard.

Example 24: Diethylamine Formylation Reaction Catalyzed by Using One of Ten Thousand of Molar Equivalent of Ruthenium Complex 1a

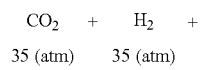

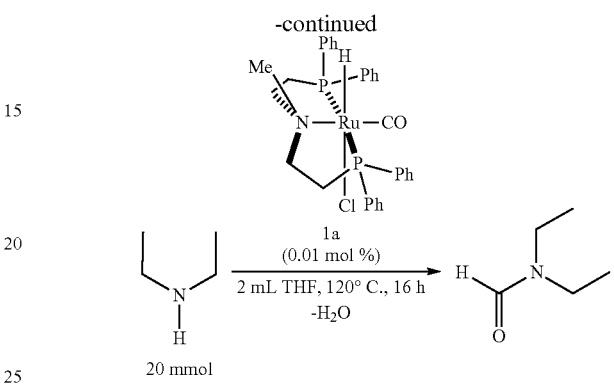

Under a nitrogen atmosphere in a glove box, Ruthenium complex 1a (1.2 mg, 0.002 mmol), tetrahydrofuran (2 ml) and diethylamine (1.342 g, 20 mmol) were added to a 125-mL Parr autoclave. The autoclave was sealed and taken out from the glove box, carbon dioxide and hydrogen were added at 35 atm separately. After a few minutes the total pressure was stably maintained at 60 atm. The mixture in reactor was heated and stirred in an oil bath at 120° C. for 16 hours and then cooled to room temperature in a water bath, and the remaining gas was slowly released in a fume hood to obtain a clear solution. The resulting mixture was filtered through a short silica gel column (ca. 2 cm) and washed with ethyl acetate (5 mL×3). The resulting filtrate was dried over anhydrous sodium sulfate and the solvent was removed by distillation in vacuo to give N, N-diethylamide as a colorless liquid (0.860 g) in 54% yield.

1H NMR (400 MHz, $CDCl_3$) δ 8.05 (s, 1H), 3.37 (q, J=6.8 Hz, 2H), 3.28 (q, J=6.8 Hz, 2H), 1.20 (t, J=7.2 Hz, 3H) 1.14 (t, J=6.8 Hz, 3H) ppm.

Example 25: Di(n-Butylamine) Formylation Reaction Catalyzed by Using One of Ten Thousand of Molar Equivalent of Ruthenium Complex 1a

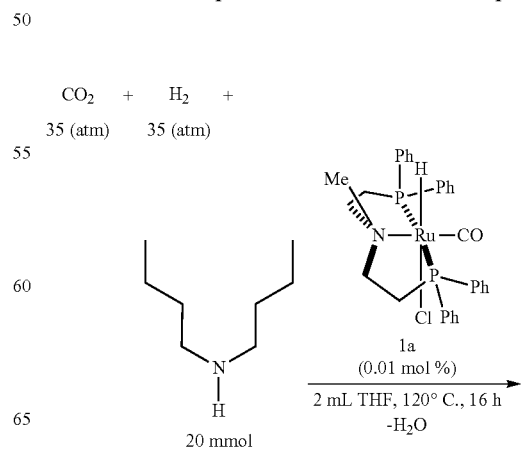

-continued

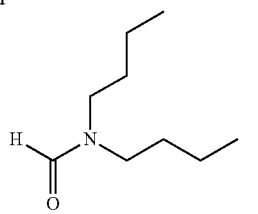

Steps similar to those in example 24 were employed, ruthenium complex 1a (1.2 mg, 0.002 mmol) was used as catalyst, and a reaction among di-n-butylamine (2.585 g, 20 mmol) and $CO_2$ and $H_2$ (each at a pressure of 35 atm) was performed in a 125-mL Parr autoclave at 120° C. in an oil bath for 16 hours. N, N-dibutylformamide was separated and obtained as a colorless liquid (2.790 g) in 89% yield.

$^1$H NMR (400 MHz, CDCl$_3$) δ 8.04 (s, 1H) 3.29 (t, J=7.2 Hz, 2H), 3.19 (t, J=7.2 Hz, 2H), 1.54-1.47 (m, 4H), 1.35-1.28 (m, 4H), 0.96-0.92 (m, 6H) ppm.

Example 26: N-Methylbutylamine Formylation Reaction Catalyzed by Using One of Ten Thousand of Molar Equivalent of Ruthenium Complex 1a

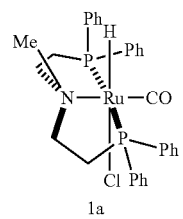

Steps similar to those in example 24 were employed, ruthenium complex 1a (1.2 mg, 0.002 mmol) was used as catalyst, and a reaction among N-methylbutylamine (1.745 g, 20 mmol) and $CO_2$ and $H_2$ (each at a pressure of 35 atm) was performed in a Parr autoclave at 120° C. in an oil bath for 16 hours. N-methylbutylformamide was to separated and obtained as a colorless liquid (2.237 g) in 97% yield. 1H NMR (400 MHz, CDCl$_3$) δ 8.04 (major rotamer, s, 0.56H), 8.02 (minor rotamer, s, 0.25H), 3.32 (minor rotamer, t, J=7.6 Hz, 0.68H), 3.23 (major rotamer, t, J=7.6 Hz, 1.26H), 2.93 (minor rotamer, s, 1.0H), 2.86 (major rotamer, s, 1.80H), 1.58-1.50 (m, 2H), 1.36-1.28 (m, 2H), 0.96-0.92 (m, 3H) ppm.

Example 27: Ethylene Glycol Amine Formylation Reaction Catalyzed by One of Ten Thousand of Molar Equivalent of Ruthenium Complex 1a

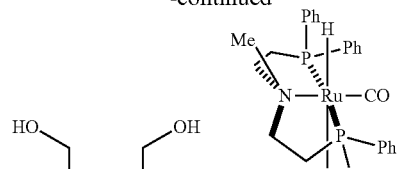

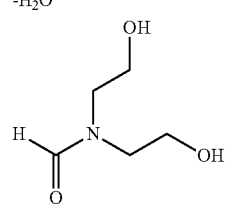

Steps similar to those in example 24 were employed, ruthenium complex 1a (1.2 mg, 0.002 mmol) was used as catalyst, and a reaction among ethylene glycol amine (2.782 g, 20 mmol) and $CO_2$ and $H_2$ (each at a pressure of 35 atm) was performed in a Parr autoclave at 120° C. in an oil bath for 16 hours. N, N-di(2-ethanolformamide was separated and obtained as a colorless liquid (2.782 g) in 99% yield.

$^1$H NMR (400 MHz, CDCl$_3$) δ8.13 (s, 1H), 3.88 (t, J=4.8 Hz, 2H), 3.76 (t, J=4.8 Hz, 2H), 3.52 (t, J=4.8 Hz, 2H), 3.42 (t, J=4.8 Hz, 2H) ppm.

$^{13}$C NMR (100 MHz, CDCl$_3$) δ164.9, 60.0, 59.9, 52.0, 47.1 ppm.

Example 28: N-Methylbenzylamine Formylation Reaction Catalyzed by Using One of Ten Thousand of Molar Equivalent of Ruthenium Complex 1a

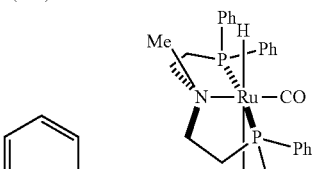

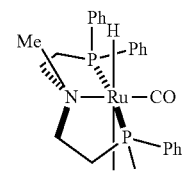

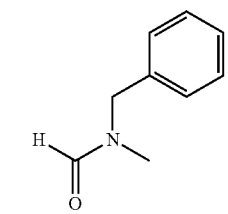

Steps similar to those in example 24 were employed, ruthenium complex 1a (1.2 mg, 0.002 mmol) was used as catalyst, and a reaction among N-methylbenzylamine (2.424 g, 20 mmol) and CO$_2$ and H$_2$ (each at a pressure of 35 atm) was performed in a Parr autoclave at 120° C. in an oil bath for 16 hours. N-methylbenzylamine was separated and obtained as a colorless liquid (2.831 g) in 95% yield. $^1$H NMR (400 MHz, CDCl$_3$) δ 8.28 (major rotamer, s, 0.53H), 8.16 (minor rotamer, s, 0.40H), 7.39-7.19 (m, 0.9H), 4.52 (minor rotamer, s, 1.16H), 4.39 (major rotamer, s, 2H), 2.84 (minor rotamer, s, 1.34H), 2.78 (major rotamer, s, 1.62H) ppm. $^{13}$C NMR (100 MHz, CDCl$_3$) δ 162.7 (major rotamer), 162.5 (minor rotamer), 136.0 (minor rotamer), 135.8 (major rotamer), 128.9, 128.7, 128.2, 128.0, 127.6, 127.4, 53.4 (major rotamer), 47.8 (minor rotamer), 34.0 (major rotamer), 29.4 (minor rotamer) ppm.

Example 29: n-Butylamine Formylation Reaction Catalyzed by Using One of Ten Thousand of Molar Equivalent of Ruthenium Complex 1a

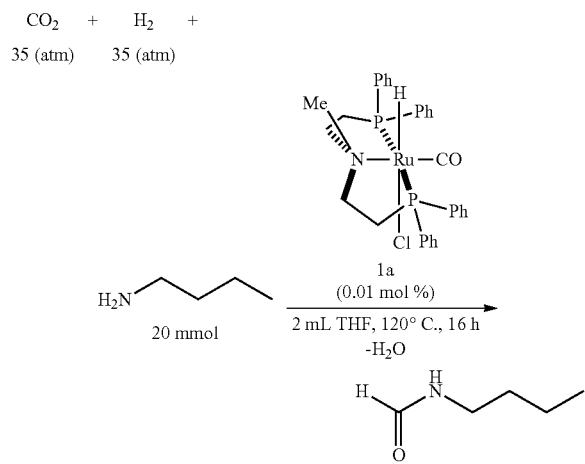

Steps similar to those in example 24 were employed, ruthenium complex 1a (1.2 mg, 0.002 mmol) was used as catalyst, and a reaction among n-butylamine (1.470 g, 20 mmol) and CO$_2$ and H$_2$ (each at a pressure of 35 atm) was performed in a Parr autoclave at 120° C. in an oil bath for 16 hours. N-n-butylformamide was separated and obtained as a colorless liquid (1.532 g) in 76% yield.

$^1$H NMR (400 MHz, CDCl$_3$) δ 8.17 (major isomer, s, 0.73H), 8.05 (minor isomer, d, J=12.0 Hz, 0.20H), 5.64 (s, br, 1H), 3.33-3.28 (major isomer, m, 1.55H), 3.23-3.21 (minor isomer, m, 0.41H), 1.55-1.48 (m, 2H), 1.41-1.34 (m, 2H), 0.95-0.91 (m, 3H) ppm.

$^{13}$C NMR (100 MHz, CDCl$_3$) δ 164.9 (minor isomer), 161.2 (major isomer), 41.5 (minor isomer), 37.8 (major isomer), 33.1 (minor isomer), 31.3 (major isomer), 19.9, 13.6 ppm.

Example 30: n-Heptylamine Formylation Reaction Catalyzed by Using One of Ten Thousand of Molar Equivalent of Ruthenium Complex 1a

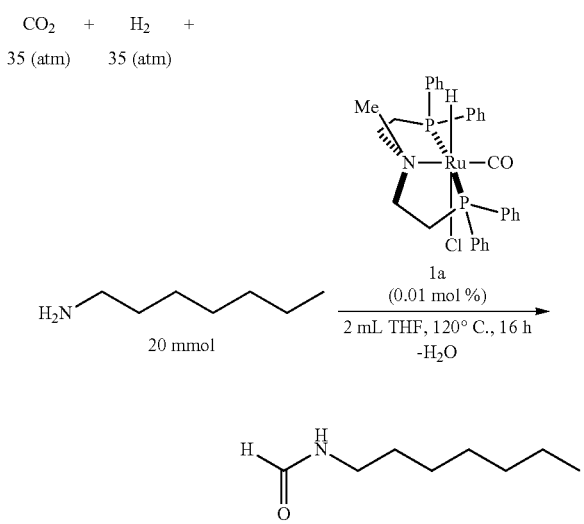

Steps similar to those in example 24 were employed, ruthenium complex 1a (1.2 mg, 0.002 mmol) was used as catalyst, and a reaction among n-heptylamine (2.30 g, 20 mmol) and CO$_2$ and H$_2$ (each at a pressure of 35 atm) was performed in a Parr autoclave at 120° C. in an oil bath for 16 hours. N-n-heptylformamide was separated and obtained as a colorless liquid (2.615 g) in 91% yield.

$^1$H NMR (400 MHz, CDCl$_3$) δ 8.16 (major isomer, s, 0.75H), 8.04 (minor isomer, d, J=12.0 Hz, 0.25H), 5.69 (s, br, 1H), 3.32-3.27 (m, major isomer, 1.52H), 3.24-3.19 (m, minor isomer, 0.48H), 1.58-1.47 (m, 2H), 1.37-1.22 (m, 8H), 0.92-0.84 (m, 3H) ppm.

$^{13}$C NMR (100 MHz, CDCl$_3$) δ 161.1, 38.2, 31.7, 29.5, 28.9, 26.8, 22.5, 14.0 ppm.

Example 31: n-Laurylamine Formylation Reaction Catalyzed by Using One of Ten Thousand of Molar Equivalent of Ruthenium Complex 1a

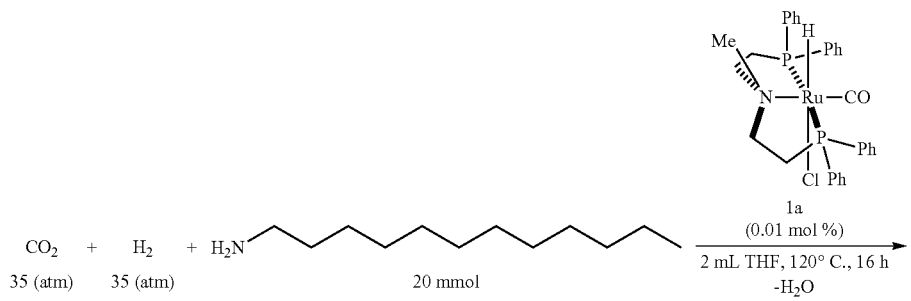

-continued

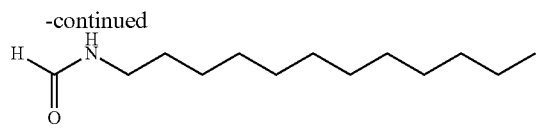

Steps similar to those in example 24 were employed, ruthenium complex 1a (1.2 mg, 0.002 mmol) was used as catalyst, and a reaction among n-laurylamine (3.725 g, 20 mmol) and $CO_2$ and $H_2$ (each at a pressure of 35 atm) was performed in a Parr autoclave at 120° C. in an oil bath for 16 hours. N-laurylformamide was separated and obtained as a white solid (4.219 g) in 91% yield.

$^1$H NMR (400 MHz, CDCl$_3$) δ 8.14 (major isomer, s, 0.68H), 8.02 (minor isomer, 0.18H) 3.28-3.19 (major isomer, m 1.83H), 2.77 (minor isomer, 0.44H), 1.59-1.46 (m, 2H), 1.37-1.18 (m, 18H), 0.92-0.80 (m, 3H) ppm.

$^{13}$C NMR (100 MHz, CDCl$_3$) δ 164.7 (major isomer) 161.3 (minor isomer), 41.8 (minor isomer), 38.2 (major isomer), 31.9 (major isomer), 31.2 (minor isomer), 29.61, 29.59, 29.54, 29.51, 29.45, 29.31, 29.22, 29.11, 26.8 (major isomer), 26.4 (minor isomer), 22.6, 14.1 ppm.

Example 32: Benzylamine Formylation Reaction Catalyzed by Using One of Ten Thousand of Molar Equivalent of Ruthenium Complex 1a

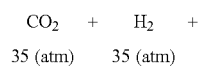

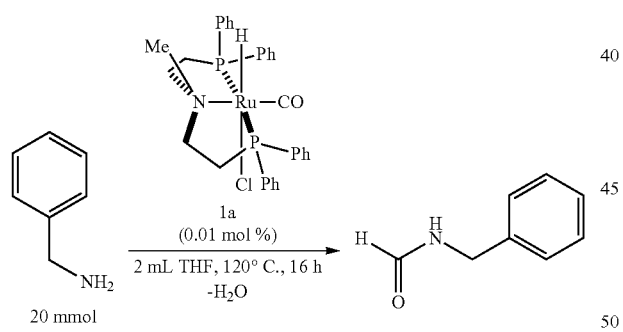

Steps similar to those in example 24 were employed, ruthenium complex 1a (1.2 mg, 0.002 mmol) was used as catalyst, and a reaction among benzylamine (2.150 g, 20 mmol) and $CO_2$ and $H_2$ (each at a pressure of 35 atm) was performed to react in a Parr autoclave at 120° C. in an oil bath for 16 hours. N-benzylformamide was separated and obtained as a white solid (2.595 g) in 96% yield.

$^1$H NMR (400 MHz, CDCl$_3$) δ 8.23 (major isomer, s, 0.77H), 8.14 (minor isomer, d, J=6.0 Hz, 0.14H), 7.37-7.24 (m, 5H), 6.10 (br, 1H), 4.48-4.45 (major isomer, m, 1.62H), 4.41-4.38 (minor isomer, m, 0.30H) ppm.

$^{13}$C NMR (100 MHz, CDCl$_3$) δ 165.0 (minor isomer), 161.6 (major isomer), 137.8, 128.8, 128.6, 127.6, 127.5, 127.0, 45.7 (minor isomer), 41.9 (major isomer) ppm.

Example 33: 2-Hydroxyethylamine Formylation Reaction Catalyzed by Using One of Ten Thousand of Molar Equivalent of Ruthenium Complex 1a

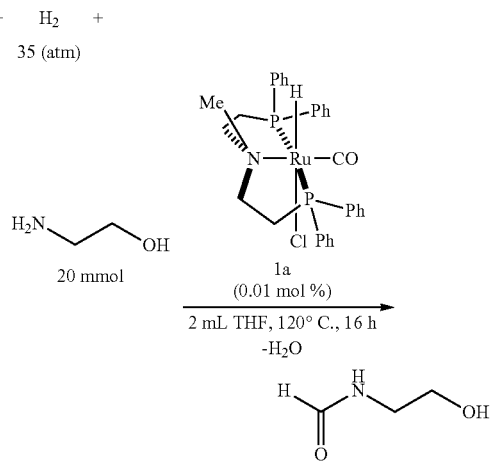

Steps similar to those in example 24 were employed, ruthenium complex 1a (1.2 mg, 0.002 mmol) was used as catalyst, and a reaction among 2-hydroxyethylamine (3.725 g, 20 mmol) and $CO_2$ and $H_2$ (each at a pressure of 35 atm) was performed in a Parr autoclave at 120° C. in an oil bath for 16 hours. N-(2-hydroxyethyl)formamide was separated and obtained as a colorless liquid (1.582 g) in 89% yield.

$^1$H NMR (400 MHz, D$_2$O) δ 7.96 (major isomer, s, 0.64H), 7.85 (minor isomer, s, 0.12H), 3.56-3.49 (m, 2H), 3.24 (t, J=4.8 Hz, 2H) ppm.

$^{13}$C NMR (100 MHz, D$_2$O) 164.5, 59.7, 39.9 ppm.

Example 34: Cyclohexylamine Formylation Reaction Catalyzed by Using One of Ten Thousand of Molar Equivalent of Ruthenium Complex 1a

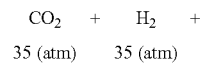

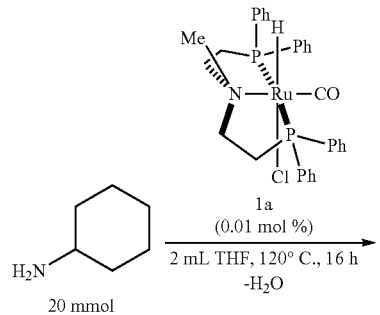

-continued

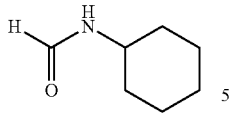

Steps similar to those in example 24 were employed, ruthenium complex 1a (1.2 mg, 0.002 mmol) was used as catalyst, and a reaction among cyclohexylamine (2.00 g, 20 mmol) and $CO_2$ and $H_2$ (each at a pressure of 35 atm) was performed in a Parr autoclave at 120° C. in an oil bath for 16 hours. N-cyclohexylamineformamide was separated and obtained as a colorless liquid (1.323 g) in 52% yield.

$^1$H NMR (400 MHz, $CDCl_3$) δ 8.14 (minor isomer, s, 0.18H), 8.11 (major isomer, s, 0.68H), 5.54 (br, 1H), 3.93-3.82 (major isomer, m, 0.74H), 3.36-3.27 (minor isomer, m, 0.30H), 2.00-1.84 (m, 2H), 1.75-1.70 (m, 2H), 1.65-1.60 (m, 1H), 1.43-1.21 (m, 5H) ppm.

Example 35: 2-Pyridylmethylamine Formylation Reaction Catalyzed by Using One of Ten Thousand of Molar Equivalent of Ruthenium Complex 1a

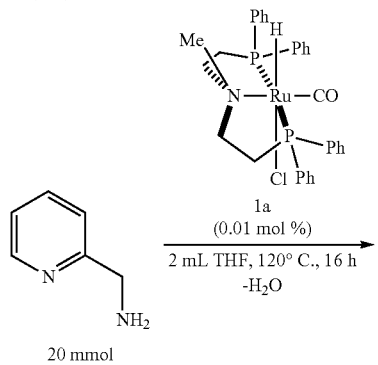

Steps similar to those in example 24 were employed, ruthenium complex 1a (1.2 mg, 0.002 mmol) was used as catalyst, and a reaction among 2-pyridylmethylamine (2.440 g, 20 mmol) and $CO_2$ and $H_2$ (each at a pressure of 35 atm) was performed in a Parr autoclave at 120° C. in an oil bath for 16 hours. N-(2-pyridyl)methylformamide was separated and obtained as a yellow liquid (2.959 g) in 96% yield.

$^1$H NMR (400 MHz, $CDCl_3$) δ 8.52 (d, J=4.8 Hz, 1H), 8.28 (major isomer, s, 0.86H), 8.25 (minor isomer, d, J=12.0 Hz, 0.1H), 7.71-7.67 (m, 1H), 7.30-7.20 (m, 2H), 4.61 (major isomer, d, J=6.0 Hz, 1.8H), 4.55 (minor isomer, d, J=6.0 Hz, 0.2H) ppm.

$^{13}$C NMR (100 MHz, $CDCl_3$) δ 165.5 (minor isomer), 161.1 (major isomer), 156.1, 148.9, 137.0, 122.5, 122.1, 47.1 (minor isomer), 43.0 (major isomer) ppm.

Example 36: 2-Methoxyethylamine Formylation Catalyzed by Using One of Ten Thousand of Molar Equivalent of Ruthenium Complex 1a

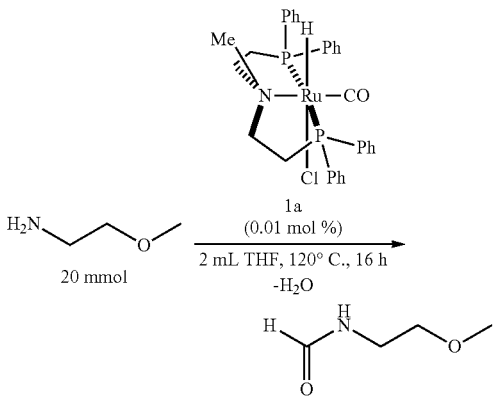

Steps similar to those in example 24 were employed, ruthenium complex 1a (1.2 mg, 0.002 mmol) was used as catalyst, and a reaction among 2-methoxyethylamine (1.502 g, 20 mmol) and $CO_2$ and $H_2$ (each at a pressure of 35 atm) was performed in a Parr autoclave at 120° C. in an oil bath for 16 hours. N-(2-methoxy)ethylformamide was separated and obtained as a colorless liquid (1.940 g) in 94% yield.

$^1$H NMR (400 MHz, $CDCl_3$) δ 8.18 (major isomer, s, 0.75H), 8.05 (minor isomer, d, J=12.0 Hz, 0.12H), 6.93 (br, 1H), 3.50-3.44 (m, 4H), 3.36 (s, 3H) ppm.

$^{13}$C NMR (100 MHz, $CDCl_3$) δ 165.2 (minor isomer), 161.6 (major isomer), 72.0 (minor isomer), 70.8 (major isomer), 58.5, 41.7 (minor isomer), 37.6 (major isomer) ppm.

Example 37: Pyrrole Formylation Reaction Catalyzed by Using One of Ten Thousand of Molar Equivalent of Ruthenium Complex 1a

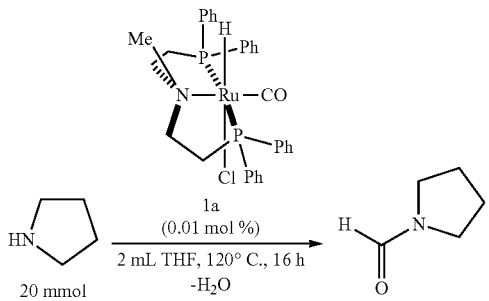

Steps similar to those in example 24 were employed, ruthenium complex 1a (1.2 mg, 0.002 mmol) was used as catalyst, and a reaction among pyrrole (1.423 g, 20 mmol) and $CO_2$ and $H_2$ (each at a pressure of 35 atm) was performed in a Parr autoclave at 120° C. in an oil bath for 16 hours. N-formylpyrrole was separated and obtained as a colorless liquid (1.969 g) in 99% yield.

$^1$H NMR (400 MHz, CDCl$_3$) δ 8.26 (s, 1H), 3.50 (t, J=6.4 Hz, 2H), 3.43 (t, J=6.4 Hz, 2H), 1.95-1.89 (m, 4H) ppm.

$^{13}$C NMR (100 MHz, CDCl$_3$) δ 160.9, 46.0, 43.1, 24.9, 24.2 ppm.

Example 38: Piperazine Dicarboxylation Reaction Catalyzed by Using One of Ten Thousand of Molar Equivalent of Ruthenium Complex 1a

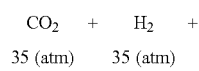

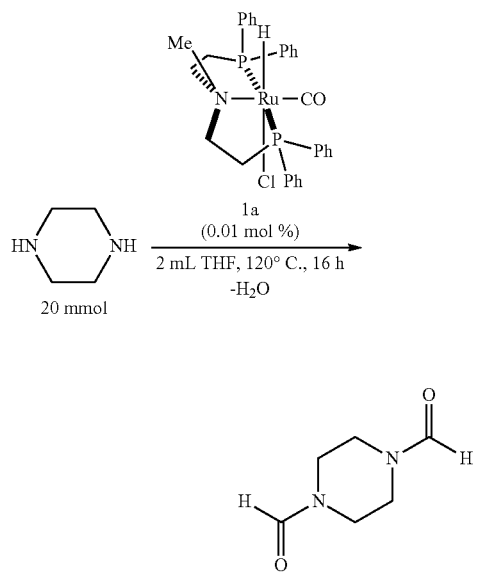

Steps similar to those in example 24 were employed, ruthenium complex 1a (1.2 mg, 0.002 mmol) was used as catalyst, 2 mL of methanol as solvent, piperazine (1.723 g, 20 mmol) and CO$_2$ and H$_2$ (each at a pressure of 35 atm) were used to react in a Parr autoclave at 120° C. in an oil bath for 16 hours. N-benzylformamide was separated and obtained as a white solid (1.969 g) in 95% yield.

$^1$H NMR (400 MHz, D$_2$O) δ 7.92 (s, 2H), 3.45-3.34 (m, 8H) ppm.

$^{13}$C NMR (100 MHz, CDCl$_3$) δ163.6, 163.5, 46.2, 46.1, 40.3, 39.3 ppm.

Example 39: Morpholine Formylation Solvent-Free Reaction Catalyzed by Using One of Fifty Thousand of Molar Equivalent of Ru Complex 1b

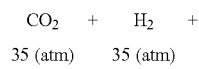

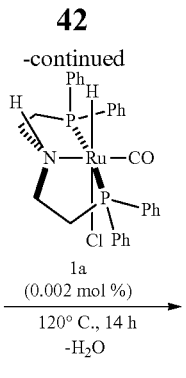

Under a nitrogen atmosphere in a glove box, Ruthenium complex 1b (0.6 mg, 0.01 mmol) and morpholine (4.404 g, 51 mmol) were added to a 125-mL Parr autoclave. The autoclave was sealed and taken out from the glove box, followed by the addition of carbon dioxide gas and hydrogen at 35 atm separately. After a few minutes, the total pressure of the gas in the autoclave was stably maintained at 60 atm. The reaction mixture in the autoclave was heated and stirred in an oil bath at 120° C. for 14 hours and then cooled to room temperature in a water bath. And then the remaining gas was slowly released in a fume hood to obtain a colorless solution. The yield of formyl morpholine was determined to be 95% by gas chromatography with p-xylene (50 μL) as internal standard.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for preparing a formamide compound, comprising
reacting an amine compound of formula I with carbon dioxide and hydrogen under the action of catalyst III to form a formamide compound of formula II: wherein the molar ratio of the amine compound of formula I to the catalyst III is 10,000-4,000,000:1; the pressure of hydrogen is 5 to 40 atmospheres, and the pressure of carbon dioxide is 5 to 40 atmospheres; and during the reaction, alkali other than amine substrate is not added;

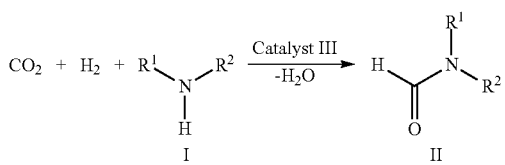

wherein
R$^1$ is hydrogen, substituted or unsubstituted C$_1$-C$_{20}$ alkyl, substituted or unsubstituted C$_4$-C$_{10}$ cycloalkyl, substituted or unsubstituted C$_6$-C$_{24}$ aryl, substituted or unsubstituted C$_7$-C$_{25}$ arylalkyl, —(CH$_2$)$_n$—OR$^3$ or —(CH$_2$)$_n$—NR$^4$R$^5$,
R$^2$ is a substituted or unsubstituted C$_1$-C$_{20}$ alkyl, substituted or unsubstituted C$_4$-C$_{10}$ cycloalkyl, substituted or unsubstituted C$_6$-C$_{24}$ aryl, substituted or unsubstituted C$_7$-C$_{25}$ arylalkyl, —(CH$_2$)—OR$^3$ or —(CH$_2$)—NR$^4$R$^5$, n is in each case independently 1-8, $R^3$, $R^4$ and $R^5$ are each independently hydrogen, substituted or unsubstituted $C_1$-$C_{20}$ alkyl, substituted or unsubstituted $C_6$-$C_{24}$ aryl, substituted or unsubstituted $C_7$-$C_{25}$ arylalkyl or heteroaryl, wherein "substituted" means that one or more hydrogen atoms of a group is substituted by hydrogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, or amido;

wherein the catalyst III is a pincer catalyst having a structure of formula III or the catalyst III has a structure of formula 2a, 2b, 2d or 3a:

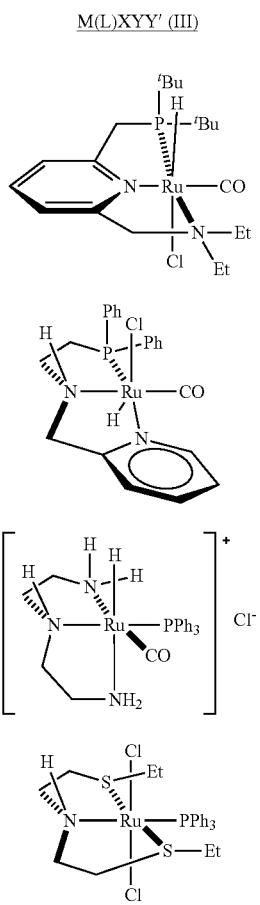

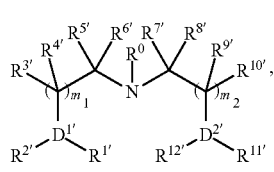

wherein
M is Fe, Co, Ni, Ru, Rh, Pd, Os, Ir, or Pt,
X, Y and Y' are each independently carbon monoxide, triphenylphosphine, pyridine, tetrahydrofuran, dimethylsulfoxide, hydrogen anion, hydroxide, chloride ion, bromide ion, iodide ion, $BH_4^-$, $BH_3CN^-$, $BH(Et)_3^-$, $BH(sec\text{-}Bu)_3^-$ or $AlH_4^-$;
L is a tridentate pincer ligand of formula IV, wherein
$m_1$ and $m_2$ are each independently an integer 1, 2 or 3;
$D^{1'}$ and $D^{2'}$ are electron donor atoms coordinated to M, which are each independently P, N or S;
$R^0$ is hydrogen, substituted or unsubstituted $C_1$-$C_{10}$ alkyl, substituted or unsubstituted $C_3$-$C_{10}$ cycloalkyl, substituted or unsubstituted $C_6$-$C_{24}$ aryl, substituted or unsubstituted $C_7$-$C_{25}$ arylalkyl, or substituted or unsubstituted $C_4$-$C_{20}$ heteroaryl;
$R^{1'}$, $R^{2'}$,
$R^{11'}$ and $R^{12'}$ are each independently hydrogen, substituted or unsubstituted $C_1$-$C_{10}$ alkyl, substituted or unsubstituted $C_3$-$C_{10}$ cycloalkyl, substituted or unsubstituted $C_6$-$C_{24}$ aryl or substituted or unsubstituted $C_4$-$C_{24}$ heteroaryl, and
$R^{3'}$, $R^{4'}$, $R^{5'}$,
$R^{6'}$, $R^{7'}$, $R^{8'}$,
$R^{9'}$ and $R^{10'}$ are each independently hydrogen, substituted or unsubstituted $C_1$-$C_{10}$ alkyl, $C_3$-$C_{10}$ cycloalkyl, substituted or unsubstituted $C_1$-$C_{10}$ alkoxy or $C_6$-$C_{36}$ aryl,
wherein "substituted" means that one or more hydrogen atoms of a group is substituted by $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, or amido.

2. The method of claim 1, wherein the catalyst III is a complex having one of the following structures:

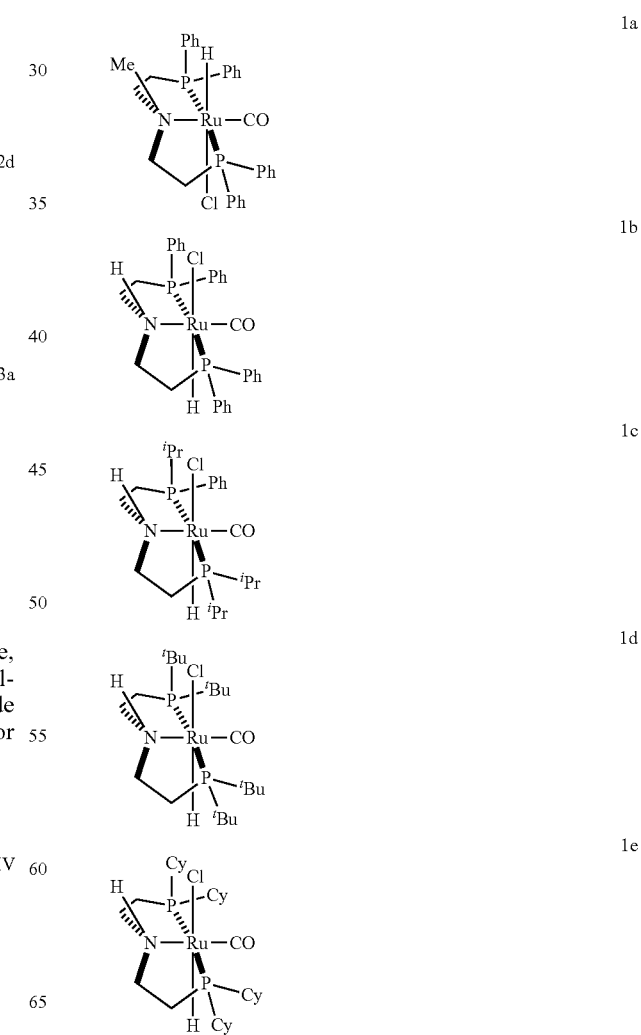

-continued

1f 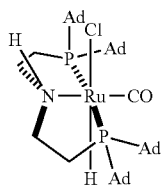

1g 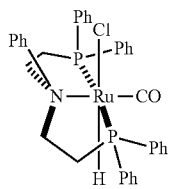

1h 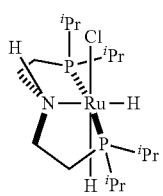

2a 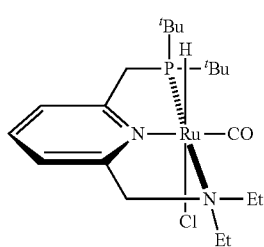

2b 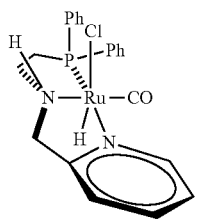

2c 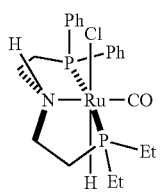

2d 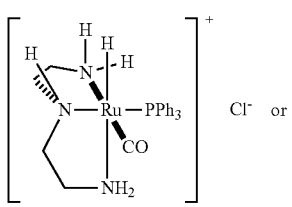

-continued

3a 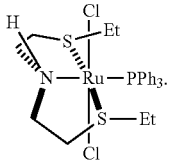

3. The method of claim 1, wherein the catalyst is a complex having one of the following structures of formula 2a, 2b, 2d or 3a:

2a 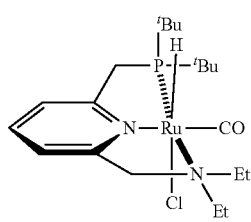

2b 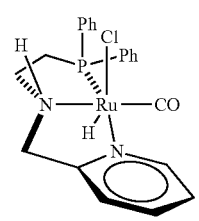

2d 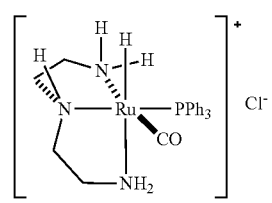

3a 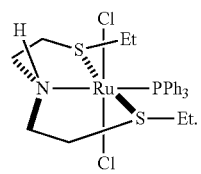

4. The method of claim 1, wherein the molar ratio of the amine compound of formula I to the catalyst is 50,000-2,500,000:1.

5. The method of claim 1, wherein the reaction time is 0.1-1000 hours.

6. The method of claim 1, wherein the pressure of hydrogen is 35 atmospheres, and/or the pressure of carbon dioxide is 35 atmospheres.

7. The method of claim 1, which is carried out at 60-200° C.

8. The method of claim 1, wherein the reaction is carried out in an organic solvent, which is DMF, tetrahydrofuran, 2-methyltetrahydrofuran, dioxane, ethylene glycol dimethyl ether, t-butyl methyl ether, benzene, toluene, xylene, methanol, ethanol, isopropanol, t-butanol, or a combination thereof.

* * * * *